United States Patent
Kawakatsu et al.

(10) Patent No.: US 8,142,717 B2
(45) Date of Patent: Mar. 27, 2012

(54) OXYGENATOR OF A HOLLOW FIBER MEMBRANE TYPE

(75) Inventors: Yuta Kawakatsu, Ohtsu (JP); Hidenori Tanaka, Ohtsu (JP); Susumu Kashiwabara, Ohtsu (JP)

(73) Assignee: Toyo Boseki Kabushiki Kaisha, Osaka-shi, Osaka (JP)

( * ) Notice: Subject to any disclaimer, the term of this patent is extended or adjusted under 35 U.S.C. 154(b) by 399 days.

(21) Appl. No.: 12/596,384

(22) PCT Filed: Apr. 21, 2008

(86) PCT No.: PCT/JP2008/057654
§ 371 (c)(1),
(2), (4) Date: Oct. 16, 2009

(87) PCT Pub. No.: WO2008/133224
PCT Pub. Date: Nov. 6, 2008

(65) Prior Publication Data
US 2010/0135852 A1  Jun. 3, 2010

(30) Foreign Application Priority Data
Apr. 23, 2007  (JP) ................. 2007-113480

(51) Int. Cl.
- *A61M 1/18* (2006.01)
- *A61M 31/00* (2006.01)
- *C08F 118/02* (2006.01)
- *C08F 220/18* (2006.01)
- *B01D 33/21* (2006.01)
- *B01D 39/00* (2006.01)

(52) U.S. Cl. ............ 422/45; 422/44; 422/48; 604/6.14; 526/319; 526/329.6; 210/500.23; 210/500.24

(58) Field of Classification Search ............ 422/45, 422/48, 44; 604/6.14; 526/319, 329.6; 210/500.23, 210/500.24
See application file for complete search history.

(56) References Cited

U.S. PATENT DOCUMENTS

| | | | |
|---|---|---|---|
| 4,770,852 A | 9/1988 | Takahara et al. | |
| 5,102,590 A | 4/1992 | Takahara et al. | |
| 6,495,101 B1 * | 12/2002 | Yokoyama et al. | 422/48 |
| 2003/0028073 A1 * | 2/2003 | Mochizuki et al. | 600/16 |
| 2003/0146150 A1 | 8/2003 | Hayashi | |
| 2006/0073467 A1 | 4/2006 | Kuno et al. | |

FOREIGN PATENT DOCUMENTS

| | | |
|---|---|---|
| JP | 62-172961 A | 7/1987 |
| JP | 01-168703 A | 7/1989 |
| JP | 05-132521 A | 5/1993 |
| JP | 07-025776 A | 1/1995 |
| JP | 11-035605 A | 2/1999 |
| JP | 11-171927 A | 6/1999 |
| JP | 11-287802 A | 10/1999 |
| JP | 11-515050 A | 12/1999 |
| JP | 2002-105136 A | 4/2002 |
| JP | 2003-111836 A | 4/2003 |
| JP | 2004-161954 A | 6/2004 |
| JP | 2004-298223 A | 10/2004 |
| JP | 2006-077136 A | 3/2006 |
| JP | 2006-124714 A | 5/2006 |
| JP | 2006-142035 A | 6/2006 |
| JP | 2006-299045 A | 11/2006 |
| WO | WO 97/14448 A1 | 4/1997 |
| WO | WO 9714448 A1 * | 4/1997 |
| WO | WO 01/66171 A1 | 9/2001 |
| WO | WO 03/106518 A1 | 12/2003 |

OTHER PUBLICATIONS

Lee et al., *Journal of Material Science: Materials in Medicine*, 10: 629-634 (1999).
Lee et al., *Biomaterials*, 11: 455-464 (Sep. 1990).
Matsuda et al., *Biomaterials*, 15(6): 417-422 (1994).
Street et al., *Journal of Polymer Science: Part A: Polymer Chemistry*, 43: 1129-1143 (2005).
Japanese Patent Office, International Search Report in International Patent Application No. PCT/JP2008/057654 (Jul. 22, 2008), English Translation.

* cited by examiner

*Primary Examiner* — Michael M Bernshteyn
(74) *Attorney, Agent, or Firm* — Leydig, Voit & Mayer, Ltd.

(57) ABSTRACT

The invention provides an oxygenator of a hollow fiber membrane type where a plurality of hollow fiber membranes are received in a housing, wherein at least a part of the regions of the hollow fiber membranes to contact blood during use is coated with a water-insoluble (meth)acrylate copolymer in which a hydrophobic (meth)acrylate is copolymerized with a hydrophilic (meth)acrylate at a molar ratio of (50 to 90):(50 to 10).

20 Claims, No Drawings

OXYGENATOR OF A HOLLOW FIBER MEMBRANE TYPE

TECHNICAL FIELD OF THE INVENTION

The present invention relates to an oxygenator of a hollow fiber membrane type which removes carbon dioxide gas in the blood and eutrophicates oxygen in the blood in extracorporeal blood circulation. More particularly, it relates to an oxygenator of a hollow fiber membrane type in which at least a part of the region of contact with the blood of the hollow fiber membrane is covered with an antithrombotic material comprising a (meth)acrylate copolymer.

BACKGROUND ART

Oxygenator of a hollow fiber membrane type using porous membrane has been widely used in general as an extracorporeal circulation device and an artificial cardiopulmonary device for auxiliary circulation in an open heart surgery for cardiac diseases. In an oxygenator of a membrane type, hollow fiber membrane is mostly used and gas exchange of the blood is conducted via the hollow fiber membrane. As a method for perfusion of the blood to an oxygenator, there are an internal perfusion method where the blood is flown to the inner side of the hollow fiber membrane while gas is flown to the outer side of the hollow fiber membrane and an external perfusion method in a reversed manner where the blood is flown to the outer side of the hollow fiber membrane while gas is flown to the inner side of the hollow fiber membrane.

In the oxygenator of an external perfusion type, the gas exchanging ability per membrane surface is higher and the loss in pressure is less than the oxygenator of an internal perfusion type whereby it has becoming the main stream. However, it has been difficult to suppress the activation of a complement system (the blood protein of immune system) caused by the result of recognition of foreign body by contacting the blood to hollow fiber membrane.

For example, an oxygenator coated with a composite of benzylalkylammonium with heparin has been disclosed (Patent Document 1). However, there is a disadvantage that the coating agent is detached into the blood during the use.

It has been also tried to cover with a hydrophilic polymer but, when porous membrane is used as a gas exchange membrane, there is a case where plasma components are permeated into the pore to cause the leakage of plasma whereupon gas exchanging ability lowers.

An oxygenator where a surface treatment with alkoxyalkyl (meth)acrylate has been disclosed as well (Patent Document 2). In preparing a coating solution of said alkoxyalkyl (meth)acrylate, the use of methanol which is a toxic substance is essential and there is a problem of elution of methanol remaining in the oxygenator into the blood and there is also a problem that long time and high cost are needed for a complete removal of methanol from the oxygenator.

Further, a water-soluble copolymer of polyethylene glycol (meth)acrylate and alkyl(meth)acrylate has been known (Patent Document 3). With this technique, protection of a surface of a solid phase can be performed in immunoassay. However, since this copolymer is water-soluble, long-term maintenance of biocompatibility was difficult.

In the synthesis of polymers, re-precipitation has been most easily and conveniently used as a method for the separation of low-molecular substances (such as monomer and oligomer) from copolymer, polymer, etc. However, no method for purification of (co)polymer by means of re-precipitation from a mixture of hydrophilic monomer, hydrophobic monomer and water-insoluble (co)polymer has been known yet.

As to a method of applying a (co)polymer to medical devices, a method where the (co)polymer is dissolved in an organic solvent such as ethanol, tetrahydrofuran or acetone and the resulting solution is applied to the medical device following by drying has been generally known. However, a medical tube made of, for example, plasticized polyvinyl chloride contains a phthalate as a plasticizer and, when an organic solvent solution is contacted, the plasticizer is easily dissolved out and the tube hardens or the tube itself is swollen whereupon deformation or crack is resulted. Thus, that has a problem in terms of quality of the product.

As to a water-insoluble polymer which is compatible with the blood, a copolymer of alkoxyalkyl acrylate with alkyl (meth)acrylate has been known but, in that case, a specific copolymer is used (Patent Documents 4 and 5).

It has been also known that a copolymer containing a vinyl monomer having ethylene glycol chain in a molecule is used for a specific use which is a dispersing agent for a suspension polymerization (Patent Document 4) and, further, a copolymer containing a unsaturated polymerizing monomer of ethylene type having an acrylic alkylene glycol residue and the use of a biochip material using said copolymer (i.e. a polymer compound which fixes a physiologically active substance) have been known as well (Patent Document 6).

A biocompatible composition comprising a nonionic polymer having a glass transition point of not higher than 300K and an organism-derived material having an anticoagulant activity has been known (Patent Document 7). However, since an organism-derived material is an essential ingredient in this composition, no consideration is done for the problems of infection and safety.

There has been known a product where alkoxyalkyl (meth) acrylate is subjected to a surface treatment to a part where an oxygenator of a hollow fiber membrane external perfusion type contacts with the blood (Patent Document 2). However, since this (meth)acrylate has a more hydrophilicity, there is a risk that it is easily eluted into the blood.

There has been known an art where adsorption of protein is suppressed by a copolymer of methoxy polyethylene oxide methacrylate with alkyl methacrylate (Nonpatent Document 1). However, since this copolymer has a more hydrophilicity, there is a problem that it is dissolved in the blood.

As a coating material for suppressing the adsorbed amount of protein, a copolymer of methyl methacrylate with methoxy polyethylene oxide methacrylate has been known (Nonpatent Document 2). However, since hydrophobicity is resulted using methyl methacrylate where carbon number of the alkyl group is 1, polyethylene glycol chain is unable to be sufficiently introduced whereby there is a problem that no sufficient compatibility with blood is able to be achieved.

A surface treating agent for medical devices comprising a hydrophilic-hydrophobic block copolymer has been known (Nonpatent Document 3). However, since this copolymer has a more hydrophilicity and is easily eluted into the blood, there is a problem that the effect does not continue for a long period of time.

A block copolymer of oligoethylene glycol methacrylate with octadecyl acrylate has been known (Nonpatent Document 4). However, since the copolymer is solid at room temperature, there is a problem that, after the coating is done, it is physically detached from the medical device.

There has been known a filter agent by which leucocytes are selectively removed where the agent comprises a copolymer of methoxy polyethylene glycol methacrylate with methyl methacrylate (Patent Document 8). However, since this copolymer has a more hydrophilicity and is easily eluted into the blood, there is a problem that the effect does not continue for a long period of time.

There has been known a biocompatible lubricant hydrophilic material comprising a copolymer of methoxy polyethylene glycol methacrylate with alkyl methacrylate (Patent Document 9). However, since this copolymer has a more hydrophilicity and is easily eluted into the blood, there is a problem that the effect does not continue for a long period of time.

There has been known a copolymer comprising methoxy polyethylene glycol (meth)acrylate with alkyl (meth)acrylate (Patent Document 10). However, since the copolymer is solid at room temperature, there is a problem that, after the coating is done, it is physically detached from the medical device.

There has been known an antithrombotic surface treating agent comprising alkoxyalkyl (meth)acrylate (Patent Documents 5 and 11). However, since this copolymer has a more hydrophilicity and is easily eluted into the blood, there is a problem that the effect does not continue for a long period of time.

NONPATENT DOCUMENTS

1. Biomaterials, 1990, 11(7), 455-464
2. Journal of Materials Science: Materials in Medicine, 1999, 10(10/11), 629-634
3. Biomaterials, 1994, 15(6), 417-422
4. Journal of Polymer Science, Part A: Polymer Chemistry, 2005, 43(5), 1129-1143

PATENT DOCUMENTS

1. Japanese Patent Application Laid-Open (JP-A) No. 172961/87
2. Japanese Patent Application Laid-Open (JP-A) No. 2006-142035
3. Japanese Patent Application Laid-Open (JP-A) No. 287802/99
4. Japanese Patent Application Laid-Open (JP-A) No. 2004-161954
5. Japanese Patent Application Laid-Open (JP-A) No. 2003-111836
6. Japanese Patent Application Laid-Open (JP-A) No. 2006-299045
7. Japanese Patent Application Laid-Open (JP-A) No. 2004-298223
8. Japanese Patent Application Laid-Open (JP-A) No. 25776/95
9. Japanese Patent Application Laid-Open (JP-A) No. 515050/99
10. Japanese Patent Application Laid-Open (JP-A) No. 2006-77136
11. Japanese Patent Application Laid-Open (JP-A) No. 2002-105136

Even when each of the above-mentioned prior art is considered, it is the actual current status that no publication where the technical matter which is able to clearly disclose the treating liquid for medical materials of the present invention has been found yet.

DISCLOSURE OF THE INVENTION

Problem that the Invention is to Solve

An object of the present invention is to provide an oxygenator of a hollow fiber membrane type having a good compatibility with the blood and a high safety or, in other words, said lung where the thin membrane formed in a hollow fiber membrane form does not inhibit the permeability of oxygen and carbon dioxide gas, eluted thing and the like from the coat to the blood are small, sufficient physical strength being durable for use is available, activation of complement system and coagulation system is low, adhesion of platelets is low and plasma leakage (wet lung) is low whereby the blood is not damaged.

Means for Solving the Problem

When an artificial material contacts organism (blood), various bioreactions are induced. Examples of the initial reactions of the organisms to the material include activation of complements, coagulation of blood and activation of platelets and all of them take place as a result that the organism recognizes the artificial material as a foreign matter. It has been said that, in general, when hydrophilicity of the material is high, degree of activation of complements is high as well. On the contrary, with regard to the platelet adhesion, there is a tendency that, when hydrophilicity of the material is high, adhesion and activation are suppressed. The present inventors have conducted various investigations for the suppression of both complement activation and platelet activation.

In order to solve the above problems, the present inventors have conducted intensive investigations and, as a result, they have found a method of coating a copolymer (antithrombotic material) to medical materials where suppression of both complement activation and platelet activation is achieved and no leakage of plasma happens as well whereupon they have accomplished the present invention.

Thus, the present invention has the following characteristic features.

(1) An oxygenator of a hollow fiber membrane type where a plurality of hollow fiber membranes are received in a housing, characterized in that at least a part of the regions of contact with the blood of the hollow fiber membrane is coated with a water-insoluble (meth)acrylate copolymer in which a hydrophobic (meth)acrylate is copolymerized with a hydrophilic (meth)acrylate at a molar ratio of (50 to 90):(50 to 10) (hereinabove, the term "water-insoluble" means that, when 1% by weight of the (meth)acrylate copolymer is allowed to stand for 30 days in 99% by weight (to said copolymer) of a physiological saline solution of 37° C., a weight reduction ratio of said copolymer is not more than 1% by weight).

(2) The oxygenator of a hollow fiber membrane type wherein the hydrophobic (meth)acrylate contains alkyl (meth)acrylate represented by the following general formula 1.

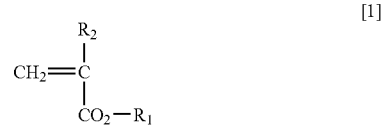

[1]

(In the formula, $R_1$ represents an alkyl group or aralkyl group having 6 to 18 carbon atoms, and $R_2$ represents a hydrogen atom or a methyl group.)

(3) The oxygenator of a hollow fiber membrane type wherein the hydrophilic (meth)acrylate contains methoxy polyethylene glycol (meth)acrylate represented by the following general formula 2.

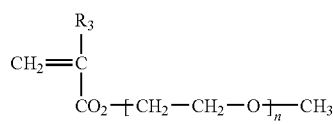

[2]

(In the formula, $R_3$ represents a hydrogen atom or a methyl group, and n represents 2 to 1,000.)

(4) The oxygenator of a hollow fiber membrane type wherein it is an internal perfusion type in which the water-insoluble (meth)acrylate copolymer coating is formed in the inner surface of the hollow fiber membrane through which the blood passes.

(5) The oxygenator of a hollow fiber membrane type wherein it is an external perfusion type in which the water-insoluble (meth)acrylate copolymer coating is formed in the outer surface of the hollow fiber membrane through which the blood passes.

(6) The oxygenator of a hollow fiber membrane type wherein the number-average molecular weight of the water-insoluble (meth)acrylate copolymer comprising the hydrophobic (meth)acrylate and the hydrophilic (meth)acrylate is from 2,000 to 200,000.

Advantages of the Invention

In the oxygenator of the present invention, at least a part of the region of contact with the blood of the hollow fiber membrane is coated with a (meth)acrylate copolymer comprising a hydrophobic monomer and a hydrophilic monomer having an antithrombotic property and, therefore, activation of complement system and coagulation system is low. In addition, said copolymer is not substantially present in the region of the oxygenator which does not contact with the blood and, therefore, the region of the oxygenator which does not contact with the blood maintains the hydrophobic state of the constituting materials for the oxygenator whereby leakage of the plasma is very low.

BEST MODE FOR CARRYING OUT THE INVENTION

In the oxygenator of a hollow fiber type of the present invention, its shape is not particularly limited so far as a plurality of hollow fiber membranes for exchanging the gas are received in a housing and may be any of cylinder, cuboid, etc. In addition, it may be an external perfusion type where the blood is flown in the outer side of the hollow fiber while oxygen gas is flown in the hollow region of the hollow fiber membrane or may be an internal perfusion type where the blood is flown in the hollow region of the hollow fiber while oxygen gas is flown in the outer side of the hollow fiber membrane.

The hollow fiber membrane constituting the above oxygenator is a porous membrane in which inner diameter is 100 to 1,000 μm, membrane thickness is 5 to 500 μm, vacancy factor is 5 to 90% and pore size is 0.01 to 5 μm, preferably 0.01 to 1 μm. As to a material used for the porous membrane, a hydrophobic polymer material such as polypropylene, polyethylene, polysulfone, polyacrylonitrile, polytetrafluoroethylene or cellulose acetate may be used. Among them, that which comprises polyolefin resin such as polypropylene, polyethylene or poly-4-methylpentene-1 is more preferred.

In the above oxygenator, the filling factor of the hollow fiber membrane to the space in the housing is preferred to be 40 to 85%. As a result of making the filling factor as such, linear velocity of the blood is optimized and it is now possible to suppress the coating amount of the copolymer of the present invention on the oxygenator material to a minimum extent particularly in the case of an oxygenator of an external perfusion type. It is also preferred that the distance of the adjacent hollow fiber membranes in the housing is 1/10 to 1/1 to the outer diameter of the hollow fiber membrane. More preferably, the distance of the adjacent hollow fiber membranes is 30 to 200 μm. When the distance as such is secured, there are advantages that workability in coating the copolymer of the present invention to the region of contact to the blood after assembling the oxygenator is enhanced and that coating spots are able to be suppressed. In addition, in the case of an external perfusion type, there is another advantage that the effect of suppressing the channeling of the blood is enhanced.

In the present invention, the oxygenator housing is preferred to be formed by a hydrophobic synthetic resin such as polycarbonate, acrylic-styrene copolymer or acrylic-butylene-styrene copolymer. The housing is preferred to be, for example, a cylindrical shape and is a transparent thing. When it is formed as a transparent thing, confirmation of the inner region is able to be easily conducted.

A port region which is inlet/outlet for the blood and oxygen gas is also preferred to be formed by the above hydrophobic synthetic resin used for the housing.

As to a potting agent which adheres the hollow fiber membrane to the housing in a liquid-tight manner, it is preferred to use polyurethane resin, epoxy resin, silicone resin or the like.

It is preferred in the present invention that at least a part of the region of contact with the blood of the hollow fiber membrane is covered by a water-insoluble (meth)acrylate copolymer. Said copolymer is used for covering in order to suppress the foreign body reaction of the organism when the artificial material contacts the blood and such an object is able to be achieved when said copolymer is made to exist in at least a part of the region of contact with the blood. Further, when said copolymer is covered only said region of contact with the blood, advantages in terms of cost are enhanced such as that mere minimum cost is needed. In the case of an oxygenator of an external perfusion type, it is more preferred that not only the region of contact with the blood of the hollow fiber membrane but also at least a part of the region contact with the blood such as a housing or a potting agent for fixing the hollow fiber membrane to the housing or a port region which is an inlet/outlet for the blood is covered by said (meth) acrylate copolymer. On the other hand, even in the oxygenator of an internal perfusion type, it is more preferred that not only the region of contact with the blood of the hollow fiber membrane but also at least a part of the region of the blood port contacting with the blood is covered by said (meth) acrylate copolymer. Particularly in the case of the oxygenator of an internal perfusion type, since there are characteristics that the linear velocity of the blood is relatively high and that foreign body reaction such as production of thrombosis hardly happens, at least the region where thrombosis production is apt to happen may be covered with said polymer.

In the present invention, said copolymer may cover the region which is not in contact with the blood and, when it covers the inner surface, outer surface or pored region of the hollow fiber membrane, there is a possibility that leakage of the plasma is resulted when blood is flown whereby it is preferred to cover only the region of contact with the blood of the hollow fiber membrane. Due to such a reason, it is preferred in the present invention that the copolymer is not substantially present in the region of non-contact with the blood.

The wording reading "is not substantially present" means, for example, the state where the region of non-contact with the blood of the hollow fiber membrane retains the hydrophobic characteristics of the membrane material itself whereby leakage of the plasma is able to be prevented.

The hollow fiber membrane used for the oxygenator of a membrane type has a pore size of about 0.01 to 5 µm and, since the pore size is significantly big as compared with the gas molecules to be permeated, the gas molecules pass through the pores of the membrane. Accordingly, the gas permeability speed becomes also high and, further, vapor also permeates abundantly whereby there are problems that properties lower due to the dew condensation (wet lung) on the membrane surface of the gas phase side and further that, upon using for a long period of time by circulating the blood, the plasma is leaked out. The cause for the leakage of the plasma is presumably due to the fact that protein component or the like in the plasma gradually adheres onto the membrane surface whereby hydrophobicity lowers little by little and, once leakage of the plasma happens, there may be the case where gas exchanging ability of the membrane greatly lowers resulting in the state where it is no longer able to be used.

Since the antithrombotic material is a copolymer containing a hydrophilic (meth)acrylate in the present invention, it is preferred in view of preventing the wet lung that said copolymer is not present on the side of the region of non-contact with the blood on the hollow fiber membrane.

In the present invention, it is preferred to use a (meth) acrylate copolymer as a coating material for the region of contact with the blood of the oxygenator. Up to now, substances derived from organisms represented by heparin (derivative) have been utilized as a material for improving the blood compatibility of the oxygenator. However, there is a problem of infection, a problem of high cost, and a problem that long-time use is not possible due to the high solubility in the blood. In addition, as a material of a synthesized type, a material having excellent biocompatibility such as 2-methacryloyloxyethyl phosphoryl choline (MPC) or 2-methoxyethyl acrylate has been used. The (meth)acrylate copolymer of the present invention is a copolymer comprising hydrophobic (meth)acrylate and hydrophilic (meth)acrylate whereby it goes without saying that the copolymer is highly biocompatible and, moreover, the copolymer has such advantages that the balance between hydrophilicity and hydrophobicity is apt to be well controlled, that the monomer is easily available and that the synthesis is easy whereby it has a wide applicability and is preferably used.

In the oxygenator of a hollow fiber membrane type of the present invention, activation of complement system at the region of contact with the blood of the hollow fiber membrane is low and leakage of the plasma from the hollow fiber membrane is also low. Thus, since the region of contact with the blood of the hollow fiber membrane is covered by a (meth) acrylate copolymer having both hydrophilic and hydrophobic properties, activation of the complement system is low. In addition, since said (meth)acrylate copolymer is not substantially present in the region of non-contact with the blood of the hollow fiber membrane, the region of non-contact with blood of the hollow fiber membrane maintains the hydrophobic state of the oxygenator material and is equipped with the high preventing action for the leakage of the plasma.

In the present invention, it is preferred that the hydrophobic (meth)acrylate contains an alkyl (meth)acrylate represented by the following general formula 1.

According to "Acrylic Resin, Synthesis/Design and Development of New Applications, Chubu Region Development Research Center, Inc., issued in 1985" and "Acrylic Ester and Its Polymer [II], Shokodo Co., Ltd., issued in 1975", as the number of carbon atoms in alkyl (meth)acrylate is increased, the glass transition temperature of the polymer is decreased, and after reaching a minimal value, the glass transition temperature tends to increase. The minimal value is 8 carbon atoms in n-alkyl acrylate, and 12 carbon atoms in n-alkyl methacrylate. That is, it is indicated that by incorporating alkyl acrylate having 8 carbon atoms as a copolymerization component, the glass transition temperature of the copolymer can be lowered.

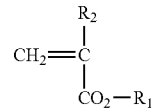

[1]

(In the formula, $R_1$ represents an alkyl group or aralkyl group having 2 to 30 carbon atoms, and $R_2$ represents a hydrogen atom or a methyl group.)

It is preferable in the present invention that as alkyl(meth) acrylate of the general formula 1, those in which $R_1$ has 2 to 30 carbon atoms, more preferably 4 to 24 carbon atoms, and further preferably 6 to 18 carbon atoms are used. Specific examples of such alkyl(meth)acrylate include normal hexyl (meth)acrylate, cyclohexyl (meth)acrylate, phenyl (meth) acrylate, benzyl (meth)acrylate, heptyl (meth)acrylate, octyl (meth)acrylate, 2-ethylhexyl (meth)acrylate, nonyl (meth) acrylate, decyl (meth)acrylate, lauryl (meth)acrylate, myristyl (meth)acrylate, palmityl (meth)acrylate, and stearyl (meth)acrylate. Among them, 2-ethylhexyl (meth)acrylate of the following general formula 3 and lauryl (meth)acrylate are particularly preferable from the viewpoints of cost and performance.

In the present invention, the hydrophilic (meth)acrylate contains methoxy polyethylene glycol (meth)acrylate represented by the following general formula 2. Since a homopolymer of methoxy polyethylene glycol (meth)acrylate has a high hydrophilicity, its compatibility with the blood is excellent but, since it is soluble in water, there is a problem that it is gradually eluted upon contact with the blood or the like for a long period of time. The present inventors have conducted intensive investigations for a material which is not only excellent in terms of compatibility with the blood but also durable for the long-time use and, as a result, they have found that such a problem is able to be solved when appropriate hydrophobicity for preventing the elution into the blood or the like and flexibility for preventing the physical exfoliation of the coating are given to the copolymer.

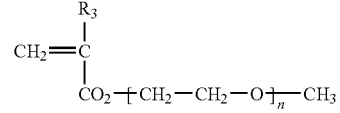

[2]

(In the formula, $R_3$ represents a hydrogen atom or a methyl group, and n represents 2 to 1,000.)

It is preferable in the present invention that as methoxy-polyethylene glycol (meth)acrylate of the following general formula 2, those having 2 to 1,000 ethylene oxide repeating units are used. More preferably those having 2 to 500, further preferably 2 to 50, still further preferably 2 to 10, and particularly preferably 2 to 5 ethylene oxide repeating units are used. Specific examples thereof include methoxydiethylene glycol (meth)acrylate, methoxytriethylene glycol (meth)acrylate, methoxytetraethylene glycol (meth)acrylate, methoxypentaethylene glycol (meth)acrylate, methoxyhexaethylene glycol (meth)acrylate, methoxyheptaethylene glycol (meth)acrylate, methoxyoctaethylene glycol (meth)acrylate, methoxynonaethylene glycol (meth)acrylate, and methoxydecaethylene glycol (meth)acrylate. When the number of a repeating unit becomes large and hydrophilicity is increased too much, even though copolymerization is performed, solubility into blood becomes high, and thus, there is a possibility of disappearing of copolymer from a medical material. Therefore, methoxytetraethylene glycol (meth)acrylate having 4 ethylene oxide repeating units and methoxytriethylene glycol (meth)acrylate having 3 ethylene oxide repeating units as shown in the following general formula 4 are preferable.

Specific examples of the representative one belonging to the water-insoluble (meth)acrylate copolymer include a copolymer of combination of the alkyl (meth)acrylate of the general formula 1 with monomer of the methoxy polyethylene glycol (meth)acrylate of the general formula 2 at a molar ratio of (30 to 90)/(70 to 10) prepared by a commonly-used polymerization method such as a copolymer of n-hexyl (meth)acrylate with methoxy diethylene glycol (meth)acrylate, a copolymer of n-hexyl (meth)acrylate with methoxy triethylene glycol (meth)acrylate, a copolymer of n-hexyl (meth)acrylate with methoxy tetraethylene glycol (meth)acrylate, a copolymer of n-hexyl (meth)acrylate with methoxy hexaethylene glycol (meth)acrylate, a copolymer of cyclohexyl (meth)acrylate with methoxy triethylene glycol (meth)acrylate, a copolymer of phenyl (meth)acrylate with methoxy triethylene glycol (meth)acrylate, a copolymer of phenyl (meth)acrylate with methoxy tetraethylene glycol (meth)acrylate, a copolymer of phenyl (meth)acrylate with methoxy pentaethylene glycol (meth)acrylate, a copolymer of n-octyl (meth)acrylate with methoxy triethylene glycol (meth)acrylate, a copolymer of n-octyl (meth)acrylate with methoxy tetraethylene glycol (meth)acrylate, a copolymer of 2-ethylhexyl (meth)acrylate with methoxy diethylene glycol (meth)acrylate, a copolymer of 2-ethylhexyl (meth)acrylate with methoxy triethylene glycol (meth)acrylate, a copolymer of 2-ethylhexyl (meth)acrylate with methoxy tetraethylene glycol (meth)acrylate, a copolymer of lauryl (meth)acrylate with methoxy triethylene glycol (meth)acrylate, a copolymer of n-nonyl (meth)acrylate with methoxy diethylene glycol (meth)acrylate, a copolymer of n-nonyl (meth)acrylate with methoxy triethylene glycol (meth)acrylate, a copolymer of n-nonyl (meth)acrylate with methoxy tetraethylene glycol (meth)acrylate, a copolymer of n-nonyl (meth)acrylate with methoxy hexaethylene glycol (meth)acrylate, a copolymer of n-decyl (meth)acrylate with methoxy triethylene glycol (meth)acrylate, a copolymer of stearyl (meth)acrylate with methoxy triethylene glycol (meth)acrylate, a copolymer of stearyl (meth)acrylate with methoxy hexaethylene glycol (meth)acrylate, a copolymer of myristyl (meth)acrylate with methoxy triethylene glycol (meth)acrylate, although the present invention is not limited thereto. When the polymerizing conditions for the copolymer and the characteristics as a medical material are taken into consideration, a product prepared by copolymerization so as to make their molar ratio (50 to 80)/(50 to 20) and to make the number-average molecular weight 2,000 to 200,000 is optimum.

When the use as a medical material is taken into consideration, a product which is purified so as to make the unreacted monomer not more than 5 molar % is suitable.

It is preferable in the present invention that hydrophobic (meth)acrylate and hydrophilic (meth)acrylate is copolymerized at a molar ratio of (30 to 90)/(70 to 10). When the amount of hydrophobic (meth)acrylate is too small, the copolymer is easily dissolved in blood, water or the like, and when the amount is too large, there is a possibility that blood compatibility derived from hydrophilic (meth)acrylate cannot be sufficiently exerted. Therefore, the molar ratio is more preferably (40 to 90)/(60 to 10), further preferably (45 to 85)/(55 to 15), and still further preferably (50 to 80)/(50 to 20).

In the present invention, the (meth)acrylate copolymer containing the hydrophobic (meth)acrylate and the hydrophilic (meth)acrylate is preferred to be substantially insoluble in water. The wording of "substantially insoluble in water" used herein means that, when the (meth)acrylate copolymer in an amount of 1% by weight is allowed to stand for 30 days in a physiological saline of 37° C. in an amount of 99% by weight (to said copolymer), the weight reduction ratio of said copolymer is not more than 1% by weight. As a result of the fact that the copolymer is substantially insoluble in water, elution of said copolymer into the blood or the like can be prevented even when the copolymer is contacted the tissue of organisms, the blood, etc.

It is preferable in the present invention that a number-average molecular weight of the (meth)acrylate copolymer is 2,000 or more from the viewpoint of easiness of purification after polymerization. Further, as the molecular weight is larger, viscosity of the (meth)acrylate copolymer becomes higher, and thus, there is a subsidiary effect that adhesion with the material of the oxygenator is improved, whereby anti-thrombogenicity can be exhibited for a long period of time. Therefore, the number-average molecular weight of the (meth)acrylate copolymer is preferably 5,000 or more, and more preferably 8,000 or more. Further, setting the number-average molecular weight to 200,000 or less is preferable from the viewpoint of improving the workability when the (meth)acrylate copolymer is coated to an oxygenator, and the like. More preferably the number-average molecular weight is 100,000 or less, further preferably 50,000 or less, still further preferably 30,000 or less, and particularly preferably 18,000 or less. Herein, the number-average molecular weight indicates a value obtained by dividing a sum of molecular weights of all molecules by a molecular number, which is one of the characteristics of a polymer.

Examples of a method of measuring a number-average molecular weight include the end-group determination method, the osmotic pressure method, the vapor pressure osmometry, the vapor pressure depression method, the freezing point depression method, the ebullioscopy, and the gel permeation chromatography (GPC), and in the present invention, the gel permeation chromatography (GPC) is employed from the viewpoint of easiness of operation.

The present inventors believe that, in order to achieve both handling property of the coating liquid and stability/safety, the following requirements are to be satisfied.

The coating liquid does not dissolve medical instruments.

The coating liquid does not extract plasticizer, etc. in the medical instruments.

The coating liquid neither denatures nor deforms the medical instruments.

The copolymer does not form precipitates during the preservation period, etc.

The copolymer is neither denatured nor deteriorated during the preservation period, etc.

The coating liquid is able to be used for a coating treatment without re-preparation.

Treatment of the waste liquid after the coating treatment is easy.

Drying treatment after the coating treatment is able to be conducted easily.

When the oxygenator of a hollow fiber membrane type is covered with an antithrombotic material comprising a (meth) acrylate copolymer in the present invention, it is possible to adopt a method where a suspension in which said copolymer is dispersed in a mixed liquid comprising an organic solvent and water is used or a method where a homogeneous liquid in which said copolymer is homogeneously dissolved in an organic solvent is used.

In the former method, since said (meth)acrylate copolymer is a product where water-soluble and water-insoluble monomers are copolymerized, selection of an organic solvent in preparing the coating liquid is extremely difficult and there happens a phenomenon where, even if carbon number of said organic solvent is different by only one, the outcome is being insoluble or soluble. Also, when an organic solvent is used solely in the latter method, there may happen such a bad affection that the polymer material constituting the oxygenator, etc. is swollen or dissolved or that the plasticizer is eluted. With regard to a method of suppressing the bad affection on the oxygenator, etc., it is able to be achieved if water is used as a solvent for the copolymer but said (meth)acrylate copolymer is insoluble in water and, moreover, it is extremely difficult to homogeneously disperse said copolymer in water only. Additional problems in the case of using water are that, since it has a big surface tension as compared with an organic solvent, a uniform application of the coating liquid to the oxygenator is difficult and further that treatment of the waste liquid is not easy and drying time becomes long due to its high boiling point.

In addition, since the oxygenator is a medical instrument having the largest surface area in an artificial cardiopulmonary circuit, the effect by the coating treatment is able to be achieved to the maximum extent while, on the other hand, complete removal of the solvent contained in the coating liquid is difficult at the drying step which is conducted after the coating treatment and the residual solvent is detected upon extraction and quantification after the drying whereby, when an organic solvent or the like is used in a high concentration as said solvent, the risk in terms of safety to the organisms is worried about. A mixed liquid where water is the main ingredient and some amount of organic solvent is contained therein is used in the present invention whereupon it has been found not only that viscosity of the coating liquid becomes low and treatment of waste liquid becomes easy but also that hydrophilicity of the coating liquid is enhanced whereby a coating liquid is now hardly able to pass through the hollow fiber membrane which is hydrophobic and the basic property of the oxygenator such as a gas permeability is not lowered. As a result thereof, the present invention has now been accomplished.

It is preferable in the present invention that the (meth) acrylate copolymer is soluble in any of alcohols having 1 to 6 carbon atoms. It is more preferable that the (meth)acrylate copolymer is soluble in an alcohol having 1 to 3 carbon atoms because of easiness of drying after coating. Herein, being soluble indicates that at least 90% by weight of the (meth) acrylate copolymer dissolves within 16 hours at room temperature when 1 g of the (meth)acrylate copolymer is immersed in 10 mL of the above described alcohol at 25° C.

According to "Polymer Basic Science, Shokodo Co., Ltd., issued in 1991", when a polymer is cooled from a melting state, the polymer undergoes an excess cooled state without being crystallized and is finally in a glass state to be solidified. The transformation from the melting state to the glass state is called glass transfer, and a temperature thereof is called a glass transition temperature. The polymer loses fluidity and is in a glass state at the glass transition temperature or lower, and on the other hand, at the glass transition temperature or higher, the polymer has fluidity and is, in a manner, in a liquid state. That is, to allow the copolymer of the present invention to have flexibility, it is required that the polymer has a glass transition temperature lower than room temperature (25° C.)

The glass transition temperature of the (meth)acrylate copolymer of the present invention is preferably −100 to 20° C. More preferably the glass transition temperature is −85 to 5° C., further preferably −80 to −10° C., and still further preferably −80 to −20° C. When the glass transition temperature is too high, there is a possibility that an antithrombotic material (copolymer) is physically detached from the medical device on which the coating membrane is carried in a working environment. When the glass transition temperature is too low, fluidity of the copolymer is increased to cause a possibility of lowering workability of coating.

The copolymer of the present invention may be any of a random copolymer, a block copolymer, and a graft copolymer. Further, a copolymerization reaction itself for producing the copolymer of the present invention is not particularly limited, and known methods such as radical polymerization, ion polymerization, photo polymerization, polymerization using a macromer, and the like can be used.

As one example for producing the (meth)acrylate copolymer of the present invention, a production method by radical polymerization will be described in the following.

That is, monomers, a polymerization solvent, and an initiator are added to a reaction apparatus equipped with a reflux condenser and capable of stirring, polymerization is initiated by heating the contents after replacement with nitrogen, and the polymerization is progressed by keeping the temperature for a specific time. It is preferable to perform bubbling of nitrogen during the polymerization. It is also possible to control a molecular weight by using a chain transfer agent in combination during this polymerization. The solvent is removed from the solution after the polymerization and a crude (meth)acrylate copolymer is obtained. Subsequently, the obtained crude (meth)acrylate copolymer is dissolved in a good solvent and dropped into a poor solvent under stirring to perform a purification treatment (hereinafter, may also be referred to as a re-precipitation treatment). The purity of the (meth)acrylate copolymer is increased by repeating the purification treatment once to several times. The copolymer thus obtained is dried.

As a polymerization solvent used in copolymerization, alcohols such as methanol, ethanol, and isopropyl alcohol, organic solvents such as ethyl acetate, toluene, benzene, and methyl ethyl ketone, or water can be used. Among them, ethyl acetate, methanol, ethanol and the like are preferably used in the present invention from the viewpoints of solubility of monomers and a copolymer to be obtained and availability thereof. Further, plural kinds of the above solvents can be used in the form of a mixture. A feed weight ratio of these polymerization solvent and monomers is preferably (20 to 90)/(80 to 10), more preferably (30 to 90)/(70 to 10), and further preferably (35 to 85)/(65 to 15). When the feed ratio is within this range, the polymerization reactivity can be enhanced to the maximum.

As a polymerization initiator, peroxide-based and azo-based radical initiators generally used in radical polymerization are used. As peroxide-based radical initiators, inorganic peroxides such as potassium persulfate, ammonium persulfate, and hydrogen peroxide, and organic peroxides such as benzoyl peroxide, t-butyl hydroperoxide, and cumene peroxide are used. As azo-based radical initiators, 2,2'-azobisisobutylonitrile, 2,2'-azobis(2-aminodipropane)dihydrochloride, dimethyl 2,2'-azobisbutylate, and dimethyl 2,2'-azobis(2-methylpropionate) are used. Further, a redox initiator obtained by combining a reducing agent with a peroxide-based initiator can be also used. These polymerization initiators are preferably added in an amount of 0.01 to by weight based on monomers in a polymerization solution. More preferable amount to be added is 0.05 to 0.5% by weight, and 0.05 to 0.3% by weight is further preferable. Setting an amount to be added of the polymerization initiator, or the like within such a range enables to obtain a copolymer having an adequate number-average molecular weight in a good reactivity.

A temperature in polymerization differs depending on a kind of a solvent and a kind of an initiator, but it is preferable to employ a temperature around a temperature of a 10-hour half life period of an initiator. Specifically, 20 to 90° C. is preferable when the above described initiators are used. 30 to 90° C. is more preferable, and 40 to 90° C. is further preferable. As a chain transfer agent used for controlling a molecular weight in polymerization, thiol compounds having a high boiling point such as dodecyl mercaptan, thiomalic acid and thioglycolic acid, isopropyl alcohol, phosphorous acid, hypophosphorous acid, and the like can be used.

Since the (meth)acrylate copolymer is made by copolymerizing a hydrophilic monomer and a hydrophobic monomer in the present invention, the (meth)acrylate copolymer has both hydrophilic property and hydrophobic property. Therefore, a hydrophilic monomer (methoxypolyethylene glycol (meth)acrylate) and a hydrophobic monomer (alkyl (meth)acrylate), which are unreacted monomers, as well as oligomers consisting of these monomers and a (meth)acrylate copolymer are present in a solution after copolymerization in a mixed state. In order to isolate a water-insoluble (meth)acrylate copolymer from the mixture of these components, for example, the copolymer solution may be dropped into a re-precipitation liquid dissolving the hydrophilic monomer to perform purification, and subsequently, the copolymer may be purified by using a re-precipitation liquid dissolving the hydrophobic monomer. However, in such a combination of purification methods, there are problems that not only a purification operation is complicated, but also a purification cost increases and loss of the copolymer is large. The inventors of the present invention made intensive studies on a purification method for obtaining a (meth)acrylate copolymer with a simple and easy purification operation, and at low cost and a high recovery rate; as a result, they found out that the (meth)acrylate copolymer can be efficiently recovered by using a re-precipitation poor solvent obtained by mixing an alcohol and water at a specific ratio.

As a solvent used for purifying the copolymer by re-precipitation, a solvent that does not dissolve the copolymer but dissolves both of the hydrophilic monomer and the hydrophobic monomer is preferably used in the present invention. In order to precipitate the (meth)acrylate copolymer, when only an alcohol is used, it is required to improve or decrease hydrophilicity of the alcohol. Examples of a method of controlling hydrophilicity of the alcohol include a method of mixing an alcohol with a solvent having high hydrophilicity. Specific examples of such a solvent include water, 1,4-dioxane, tetrahydrofuran, N-methylpyrrolidone, N,N-dimethylformamide, and N,N-dimethylacetamide, and it is preferable to use water from the viewpoints of easiness of volatilization and cost. By using an alcohol and water in the form of a mixture at a specific mixing ratio as a poor solvent, hydrophilicity can be controlled and the (meth)acrylate copolymer can be obtained at a high recovery rate.

It is preferable to use an alcohol having 1 to 10 carbon atoms, more preferably 1 to 7 carbon atoms, and further preferably 1 to 4 carbon atoms as an alcohol used for a re-precipitation treatment in the present invention. Specific examples of such an alcohol include methanol, ethanol, 1-propanol, 2-propanol, 1-butanol, 2-butanol, 2-methoxy-1-propanol, and tertiary butanol. Among them, methanol, ethanol, 1-propanol, and 2-propanol are particularly preferable from the viewpoint that short time drying at low temperature is possible.

It is preferable to use an alcohol having 1 to 10 carbon atoms and water in the form of a mixture at a weight ratio of (40 to 99)/(60 to 1), more preferably (50 to 99)/(50 to 1), and further preferably (60 to 95)/(40 to 5) in the present invention. When a ratio of an alcohol is too large, the (meth)acrylate copolymer is hardly precipitated, and when a ratio of water is too large, there is a possibility that unreacted monomers are mixed in the precipitated (meth)acrylate copolymer as an impurity, and thus, the weight ratio is particularly preferably (70 to 95)/(30 to 5).

It is preferable in the present invention that a mixed liquid of an alcohol having 1 to 10 carbon atoms and water is used as a poor solvent for re-precipitation. A good solvent may be any solvent as far as it dissolves the (meth)acrylate copolymer and is miscible with the poor solvent. Specific examples thereof include tetrahydrofuran, chloroform, acetone, ethyl acetate, N,N-dimethylformamide, N,N-dimethylacetamide, and N-methylpyrrolidone. Among them, tetrahydrofuran and acetone having a low boiling point are particularly preferable from the viewpoint of being easily dried. It is preferable to purify the copolymer by repeating re-precipitation plural times in which these substances are used as a good solvent and added to the above poor solvent.

Performing the re-precipitation operation as described above 2 to 8 times as necessary makes it possible to recover a water-insoluble (meth)acrylate copolymer containing less than 5% by mol of unreacted monomer at such a high recovery rate as 50% by weight or more. When the amounts of unreacted monomer, oligomer and polymerization residue contained in said copolymer are too much, there may be the case where they are eluted into the blood causing the shock symptom, etc. of a patient. Although most of those substances are able to be removed by means of a re-precipitation purification method, the amounts of the causing substances as such are to be made not more than 5 molar % in terms of the reacting monomers when safety of the patient is taken into consideration. However, when a purification step is taken into consideration, it is preferred to be not more than 3% by mol, and preferably not more than 1% by mol. In the present invention, careful attention was paid taking the specific use (a medical material) into consideration and, as a result, a purifying step accompanied by some loss or discarding of said copolymer in the re-precipitation purification is adopted whereby a copolymer where the residual amount of unreacted monomer is about 0.06 molar % which is far less than the ideal value of 0.1 molar % is able to be provided. When it is expressed in terms of purity which is another common yardstick, it is able to provide a product of not less than 90% by weight, preferably not less than 95% by weight, particular preferably not less than 99% by weight, and further preferably not less than 99.9% by weight, in terms of the purity of the copolymer when calculated by the formula of $(W2/W1) \times 100$ which is the ratio of the weight of only copolymer ($W2$) contained in the total weight ($W1$) of the pure copolymer.

When the recovery rate of the (meth)acrylate copolymer after re-precipitation exceeds 90% by weight, there causes a possibility that the unreacted monomers are remained in the recovered product, whereas when the recovery rate falls below 50% by weight, the productivity is decreased, and thus, the recovery rate is preferably 50 to 90% by weight. Making the recovery rate 50 to 90% by weight may result in some loss or discarding of the recovery of the copolymer but that is inevitable in view of such a respect that contamination of unreacted monomer is prevented as much as possible. That is because consideration as such should be naturally carried out under the specific circumstance that it is a copolymer having both hydrophilicity and hydrophobicity suitable as the medical material.

Detailed illustration of embodiment of this re-precipitation purification method is that, for example, a solution prepared by dissolving 2 g of crude (meth)acrylate copolymer (MTEGA: 33.3 g/EHA: 50.7 g) in 2 g of tetrahydrofuran is dropped into 20 g of poor solvent (weight ratio of methanol/water was set to 85/15) under stirring using a Pasteur pipette. Then, the precipitate is subjected to decantation, and 1.60 g of the copolymer is able to be recovered in a recovery rate of about 80%. After that, a solution prepared by dissolving 1.6 of said copolymer in tetrahydrofuran of the same weight is dropped into a poor solvent and such an operation is repeated for two times with the recovery rates of about 98% by weight and about 97% by weight respectively. After that, the recovered copolymer is dried at 60° C. for 4 days under the vacuum condition of 0.1 Torr whereupon 1.52 g of pure (meth)acrylate copolymer is able to be prepared. In that case, when the recovery rate is made somewhat higher such as 95% by weight, recovering amount of the copolymer increases but, in proportion to that, there is a tendency that the residual amount of the unreacted monomer increases.

In order to use a purified copolymer as a medical material, it is necessary to remove a solvent by drying. As a drying method, for example, drying is carried out at 60° C. under a reduced pressure of 1 Torr or less continuously for 2 to 10 days, and when sufficient dryness cannot be obtained, drying with reduced pressure may be successively performed. The purity of the thus obtained (meth)acrylate copolymer is preferably 95% by mol or more. When the purity of the copolymer is 95% by mol or more, for example, in the case of using the copolymer as a coating material of medical devices as described later, materials having high safety for a medical application, such as no elution of a monomer, an oligomer, or the like into the blood, can be provided.

In the present invention, since the (meth)acrylate copolymer obtained by copolymerizing alkyl(meth)acrylate and methoxypolyethylene glycol (meth)acrylate has appropriate balance of hydrophilicity and hydrophobicity, the (meth)acrylate copolymer can be preferably used as a material which is compatible with the blood. Particularly, the copolymer can be preferably used as a material for treating medical devices and artificial organs.

In addition, the (meth)acrylate copolymer of the present invention can be used alone or two or more kinds thereof can be also used in the form of a mixture.

In the present invention, when a medical device subjected to a treatment using the (meth)acrylate copolymer is in contact with blood, it is considered that methoxypolyethylene glycol (meth)acrylate having high hydrophilicity extends to a surface and exerts antithrombogenicity, while alkyl (meth)acrylate remains around the base material to prevent blood and the medical device from being directly in contact with each other.

In the present invention, a method of confirming water insolubility of the (meth)acrylate copolymer may be an aging treatment. It is preferable to use physiological saline as an extraction solvent used in the aging treatment from the viewpoints of simplicity and improving reliability of the blood compatibility evaluation that is carried out later. The aging treatment is further preferably carried out at a constant temperature of 37° C. Since the (meth)acrylate copolymer is water-insoluble, high blood compatibility is maintained after the aging treatment.

In the present invention, examples of a method of evaluating a degree of immunity activation of the (meth)acrylate copolymer include comparison of complement values. The Mayer method of measuring CH50 makes it possible to perform a simple and rapid measurement, and furthermore, the method is preferable since a measuring kit is easily available and inexpensive (see Jinkou Zouki 23(3), p. 654-659 (1994)). By reacting the sensitized sheep erythrocytes and a complement in serum, the sensitized erythrocytes are hemolyzed. Since a hemolytic degree is lowered as the complement system is activated, the method can be advantageously used for evaluation.

As another method of the immune system evaluation of the present invention, an assay of C3a called anaphylatoxin can be mentioned. When C3a is produced in a living body, change of blood vessel permeability, contraction of smooth muscle, and histamine release by obesity cells and basophil granulocytes are caused and an inflammatory reaction is mainly generated (see The Molecular Biology of a Complement—the role in the biophylaxis-, Nankodo Co., Ltd).

A larger numerical value of C3a means that the complement system is more activated, and by comparison of the numerical values, the method can be advantageously utilized as an evaluation method.

In addition, as a method of the immune system evaluation of the present invention, quantification of the terminal complement complex (Terminal Complement Complex, hereinafter, it will be abbreviated as TCC) can be mentioned. Activation of the complement system produces a membrane affection complex (hereinafter, it will be abbreviated as MAC) resulting an effect of dissolving the target cell membrane while, on the other hand, inactivation of the dissolving effect for cell membrane of MAC by protein S controls the immune effect. As to the TCC which is produced by combination of protein S with MAC and has no ability of dissolving the cell membrane, activation degree of the complement system is able to be quantified by comparing the data thereof. Thus, it is able to be considered that the more the TCC concentration, the more the activation of the complement system.

As one method of blood compatibility evaluation of (meth)acrylate copolymer in the present invention, a fibrin gel forming experiment can be mentioned. By this technique, an activation degree of fibrinogen that is one of blood coagulation factors can be evaluated. Specifically, a reaction of gelling of fibrinogen in plasma by calcium ions to form a fibrin gel is utilized. The technique is preferable since activation of the blood coagulation system can be easily evaluated without requiring a specific measuring apparatus by measuring a time required for gelation (hereinafter referred to as a gelation time) in the calcium ion-added plasma being in contact with a sample. A longer gelation time means that an action of foreign matter recognition in blood proteins is hardly caused, which indicates high blood compatibility.

In the present invention, it is preferred that a coating liquid is such a thing where a (meth)acrylate copolymer is dispersed in a mixed liquid where at least one kind of water-soluble organic solvent and water are mixed. When a mixed liquid where water-soluble organic solvent and water are mixed is used, the outcome is not only that viscosity of said treating liquid is able to be made low but also that it is possible to homogeneously disperse the water-insoluble (meth)acrylate copolymer and to keep the dispersed state stably for a long period. Moreover, in such a treating liquid, damage and denaturation of the medical device which is a base material are able to be made minimum when relatively large amount of water is added thereto.

The water-insoluble organic solvent of the present invention is preferred to be an organic solvent having 1 to 5 carbon(s). Specific examples of the water-soluble organic solvent having 1 to 5 carbon(s) usable include methanol, ethanol, isopropyl alcohol, 1-propanol, acetone, 1-butanol, 2-butanol, 2-methyl-1-propanol, tert-butanol, tetrahydrofuran, 1,4-dioxane, N,N-dimethylformamide, N,N-dimethylacetamide and N-methylpyrrolidone and, among them, methanol, ethanol, isopropyl alcohol, 1-propanol, acetone, and tetrahydrofuran having a low boiling point and being easy for its drying after coating are particularly preferred.

Concentration of the (meth)acrylate copolymer in the coating liquid of the present invention is preferred to be 0.001 to 10% by weight. When concentration of the (meth)acrylate copolymer is too low, there is a possibility that the property is not sufficiently expressed when applied, for example, to medical devices whereby the lower limit is more preferred to be not less than 0.01% by weight. On the other hand, when the concentration is too high, viscosity of the coating liquid becomes too high and there is a risk that workability lowers and, accordingly, its upper limit is preferred to be not more than 5% by weight, not more than 3% by weight, or not more than 1% by weight.

In the present invention, the coating liquid is preferred that water-soluble organic solvent and water are used by mixing them at a weight ratio of (3 to 45)/(97 to 55). When the amount of the water-soluble organic solvent is too much, there is a risk of damage due to deformation or crack of the medical device base material and, therefore, its upper limit is more preferably not more than 37% by weight, further preferably not more than 30% by weight, and still further preferably not more than 23% by weight. On the contrary, when the amount of the water-soluble organic solvent is too small, it is not possible to homogeneously disperse the (meth)acrylate copolymer in the mixed liquid and, therefore, its lower limit is more preferred to be not less than 5% by weight.

With regard to a method for preparing a coating liquid in the present invention, there are a method where (meth)acrylate is added to and dispersed in a previously-prepared mixed liquid of water-soluble organic solvent and water with stirring and a method where a (meth)acrylate copolymer is firstly dissolved in a water-soluble organic solvent and then it is dispersed in water by adding thereto with stirring. The latter is more preferred since a homogeneous dispersing is able to be expected.

When the above treating liquid of the present invention is summarized, the region of contact with the blood of the oxygenator of a hollow fiber membrane type is treated with a treating liquid where a water-insoluble (meth)acrylate copolymer in which hydrophobic (meth)acrylate and hydrophilic (meth)acrylate comprising methoxy polyethylene glycol (meth)acrylate are copolymerized at a molar ratio of (30 to 90)/(70 to 10) is dissolved in a concentration of 0.001 to 10% by weight in a mixed solvent comprising water-soluble organic solvent and water at a weight ratio of (3 to 45)/(97 to 55).

Thus, in the present invention, the (meth)acrylate copolymer is such a thing where the water-soluble monomer and the water-insoluble monomer are copolymerized in a well-balanced manner and, accordingly, said copolymer exhibits both hydrophobicity and hydrophilicity. In that case, even when only hydrophobic organic solvent is used as a solvent for the treating liquid, the influence on the water-soluble hydrophilic monomer is unable to be neglected. On the other hand, when water is used as a solvent, it is difficult to achieve the function as a solvent since said copolymer is essentially insoluble in water and, further, there is an affection of compatibility to the hydrophobic monomer in the copolymer. As a solvent which is applicable to a treating liquid containing said copolymer having such a specific property and also as a treating liquid achieving the two surface functions (blood and medical material), a specific solvent mixture comprising an organic solvent and water is now selected as such and that is based on the finding of the present inventors.

As to the coating liquid of the present invention, a mixed solvent of a water-soluble organic solvent with water is most suitable and its mixing weight rate is preferred to be (3 to 45)/(97 to 55) after taking the influence of the organic solvent on various medical materials and particularly on hollow fiber membrane into consideration and also due to the following reasons. This mixing rate has a factor which is also related to the number-average molecular weight of the (meth)acrylate copolymer. When the molecular weight becomes as high as 300,000 and 400,000, it is predicted that the solubility in the mixed solvent also becomes bad and there is a need of making the amount of the organic solvent relatively much. However, when the influence of the organic solvent is taken into consideration, the number-average molecular weight of the (meth)acrylate copolymer is preferred to be made from 2,000 to 200,000. For example, when a coating liquid is prepared using an acrylate copolymer where the number-average molecular weight is 350,000, the mixing rate of (water-soluble organic solvent)/(water) is 55/45 and that is out of the scope of the present invention whereby the water-soluble solvent is used in a relatively large amount and the influence on the hollow fiber membrane is worried about to such an extent. The technical characteristic feature specified by the present invention has a critical range for achieving the specific object which is an oxygenator and all of the above are the technical matters related in a united manner.

Now, the technical significance of the coating liquid comprising the mixed solvent of organic solvent and water will be further illustrated as follows. Firstly, the medical material comprises various kinds of plastic materials and may contain a plasticizer or a processing aid, an additive, a polymerization residue, etc. In some cases, its shape also consists of steric and porous structure such as hollow fiber membrane. Further, when the resulting product is fragile depending upon the type of the polymer material, there is a risk that damage such as swelling, plasticization, surface breakage or deformation is generated. In the case of the copolymer used in the present invention, it is easily soluble in organic solvent while, on the other hand, it is necessary to be hardly soluble in water which is relatively friendly to medical materials.

The mixing composition will now be illustrated. Thus, when the organic solvent monotonously increases as 5% (by weight), 8%, 15%, 20%, 30% and 60%, damage of the base material becomes big as a result thereof. However, unless said copolymer has an essentially water-insoluble characteristic, there is a risk of bad affection to the organisms such as elution into the blood. Thus, when the water amount in the mixed solvent monotonously increases as 30%, 40% and 50%, the coating liquid is very friendly and shows no bad affection even if contacted the medical material whereby the evaluation for the damage of base material shows a very good result. However, the coating liquid of the present invention is equipped with the specific properties which are hydrophilicity and hydrophobicity and, when the water amount in the dispersion becomes much more, there may be a risk of resulting in an unstable mixed solvent such as suspension breakage and solution breakage. In view of the characteristic of hydrophilicity and hydrophobicity of said copolymer and the characteristic of the mixed solvent, there may be a risk that the dispersed state and the quality of the original coating liquid are not easily recovered by a simple operation such as stirring. In the coating liquid as such, there is uneasiness for the properties as the coating liquid for a medical material relating to life.

Furthermore, in the present invention, the coating liquid is that where said copolymer is dissolved therein so as to make its concentration 0.001 to 10% by weight. Thus, it is a solution in a relatively low concentration and has an advantage that it is applicable to a hollow fiber membrane relatively easily. The coating liquid is able to be prepared in any concentration such as 0.5% by weight, 1% by weight or 3% by weight and, since it has a specific object that it does not affect the oxygen gas permeability when applied to the region of contact with the blood which is a hollow fiber membrane, existence of undissolved copolymer is not only a hindrance therefor but also non-appropriate for the operation of a coating formation.

When various circumstances as mentioned above are taken into consideration, the technical characteristic features of the present invention which are number-average molecular weight of the copolymer, components in the mixed solvent of organic solvent and water, composition rate of weight ratio of (3 to 45)/(97 to 55), concentration of 0.001 to 10% by weight of said copolymer, etc. are the closely-related ranges having critical technical characteristics.

When the coating liquid is used, for example, in such a manner that the (meth)acrylate copolymer is coated on the inner surface of a medical tube, there is a case where said coating liquid itself is contacted the hollow areas of the medical tube and then the liquid is evaporated therefrom to conduct the treatment. Accordingly, it is not so preferred that said copolymer dispersed in the coating liquid is precipitated within a relatively short period. Although the situation depends upon the using form, storage period, etc. of the coating liquid, it is preferred that there does not happen such a non-homogeneous state that where, to be more specific, visible precipitate of the (meth)acrylate copolymer is generated upon being allowed to stand at room temperature for 30 days. When a mixed liquid where alcohol and water are mixed at specific ratio is used, the dispersed state of said (meth) acrylate copolymer is able to be maintained for a long period of time. Examples of said alcohol to be used by mixing with water include methanol, ethanol, isopropyl alcohol, 1-propanol, 1-butanol, 2-butanol, 2-methyl-1-propanol and tert-butanol and, among them, ethanol, isopropanol, and 1-propanol having a particularly high dispersibility for said (meth) acrylate copolymer are more preferred.

Usually, viscosity of a solution in which a polymer is dissolved increases together with an increase in the concentration of the polymer. However, when a dispersed state such as a suspended state is adopted, viscosity is able to be suppressed to relatively low even when the polymer concentration is increased and it is possible to significantly lower the viscosity of the treating liquid as compared with the solution state even in the case of the high concentration (see "Shin Kobunshi Bunko, 6, Introduction and Application of Emulsions" published by Kobunshi Kankokai). Thus, when the treating liquid of the present invention is used, the dispersed state which is, strictly speaking, a non-homogeneous state is formed whereby it is now possible to suppress the increase in viscosity by tangling of polymer molecular chains as much as possible and to suppress the lowering of the workability due to a rise in viscosity of the treating liquid to the maximum extent.

In the present invention, viscosity of the (meth)acrylate copolymer at 37° C. is preferred to be from 0.5 to 10,000 Pa·s. When the copolymer (antithrombotic material) within such a viscosity range is used, handling ability of the solution when a coating liquid is prepared is able to be made good. Further, when it is coated on the medical instruments such as artificial cardiopulmonary circuit or catheter, the adhesion between said copolymer and the medical instruments becomes excellent and the retention of antithrombotic property upon a long-term use is now possible. More preferably the viscosity range is from 10 to 5,000 Pa·s, and further preferably from 100 to 1,000 Pa·s. As such, said copolymer in the present invention is a liquid substance having a relatively high viscosity.

Since the (meth)acrylate copolymer of the present invention is liquid at room temperature, said copolymer is dissolved in an appropriate solvent such as methanol or ethanol whereupon a measurement in a simple and convenient manner using, for example, a B-type viscometer (product name: Visco Basic plus, FUNGILAB) is able to be conducted.

Now the outline of the oxygenator of the present invention will be illustrated as follows. Thus, as to a material for the membrane, a nonpolar material giving relatively little amount of eluted substance and easily resulting in a porous structure by an orientation operation such as polypropylene or polyethylene which is a mainstream substance at present is recommended. Besides the above, it is of course possible to use various kinds of multi-purpose polymers provided as a membrane material such as poly-4-methylpentene-1, polytetrafluoroethylene, polysulfone, poly(vinyl chloride) or polyester. When the copolymer of the present invention is formed as a coating, the problem of unexpected elution is able to be suppressed to a minimum extent and troublesome coating forming work is able to be suppressed to the minimum extent if the copolymer of the present invention is applied only to the region of contact with the blood whereby safety of the oxygenator, conservation of energy in the manufacture of oxygenator and significance of making the cost low are able to be enhanced. When the state of use of the hollow fiber membrane is an internal perfusion type where the blood is passed through the hollow areas of the hollow fiber membrane while oxygen is passed to outside whereupon the gas exchange is conducted, it is sufficient that the copolymer of the present invention is formed as a coating on the inner side of the hollow fiber membrane. On the other hand, when it is an external perfusion type where the blood is passed to outside of the hollow fiber membrane while oxygen is passed through the hollow areas whereupon the gas exchange is conducted, it is sufficient that the copolymer of the present invention is formed as a coating on the outside of the hollow fiber membrane.

In a method of forming a coating of the copolymer on this oxygenator, the state of use is taken into consideration and, in the case of the inner perfusion type, the coating liquid of the copolymer of the present invention may be passed through the hollow areas of the hollow fiber membrane and then the dried hollow fiber membrane bundle may be installed in the module. In the case of an external perfusion type, application may be conducted by, for example, dipping the hollow fiber membrane into the coating liquid and the dried hollow fiber membrane bundle may be installed in the module.

However, in a viewpoint of efficiency, it is recommended to conduct as follows that the oxygenator is previously assembled, the above coating liquid or the above dissolved liquid containing the (meth)acrylate copolymer is passed through the blood perfusion side of the oxygenator so that the above copolymer is covered on the region of contact with the blood and then an efficient compulsory drying means such as drying by aeration, drying by hot air, drying at reduced pressure or drying by aeration at reduced pressure is freely adopted so as to remove the mixed solvent.

EXAMPLES

The present invention will now be further specifically illustrated by using the following Examples although the present invention is not limited thereto.

In carrying out the present invention, the following polymerization method, property test and measuring method are conducted whereby the significance of the oxygenator of the present invention is confirmed.

1. Manufacture of (Co)Polymer and Preparation of Coating Liquid

Example 1

(1) Polymerization of the Copolymer

To a reaction apparatus equipped with a reflux condenser and capable of stirring, 33.3 g of methoxytriethylene glycol acrylate (hereinafter, it will be abbreviated as MTEGA) (made by SHIN-NAKAMURA CHEMICAL CO., LTD.), 50.7 g of 2-ethylhexyl acrylate (hereinafter, it will be abbreviated as EHA) (made by TOKYO CHEMICAL INDUSTRY CO., LTD.), 0.0815 g of azobisisobutyronitrile (AIBN) (made by Wako Pure Chemical Industries, Ltd.), and 84.2 g of ethanol (made by Wako Pure Chemical Industries, Ltd.) were added, and a polymerization reaction was performed under the condition of 80° C. for 20 hours. After completion of the polymerization reaction, a polymerization solvent was removed by evaporation for 4 days under the conditions of 60° C. and 1 Torr, and a crude (meth)acrylate copolymer was obtained.

(2) Re-Precipitation Purification 2 g of the obtained crude (meth)acrylate copolymer was dissolved in 2 g of tetrahydrofuran and dropped into 20 g of a poor solvent (weight ratio of methanol/water was set to 85/15) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a copolymer 1.

Comparative Example 1

Azobisisobutyronitrile (AIBN) (made by Wako Pure Chemical Industries, Ltd.) (0.125 g) was added to 95.2 g of methoxy polyethylene glycol acrylate (MPEGA; mean degree of polymerization of ethylene oxide: 9) (made by SHIN-NAKAMURA CHEMICAL CO., LTD.) and 5.1 g of ethyl acrylate (EA) (made by TOKYO CHEMICAL INDUSTRY CO., LTD.), and a polymerization reaction was performed in 250 g of isopropyl alcohol (made by TOKYO CHEMICAL INDUSTRY CO., LTD.) under the condition of 80° C. for 20 hours. After completion of the polymerization reaction, the reaction liquid was dropped into n-hexane to precipitate and the product was isolated. Purification was carried out by repeating an operation of dissolving the product in isopropyl alcohol, and dropping the mixture into n-hexane twice. The product was dried at a reduced pressure for one night and day at 60° C. to thereby obtain a copolymer 2.

Comparative Example 2

Azobisisobutyronitrile (AIBN) (made by Wako Pure Chemical Industries, Ltd.) (0.0467 g) was added to 22.3 g of 2-ethylhexyl acrylate (EHA) (made by TOKYO CHEMICAL INDUSTRY CO., LTD.), and a polymerization reaction was performed in 100 g of ethyl acetate (made by TOKYO CHEMICAL INDUSTRY CO., LTD.) under the condition of 80° C. for 20 hours. After completion of the polymerization reaction, the reaction liquid was dropped into methanol to precipitate and the product was isolated. Purification was carried out by repeating an operation of dissolving the product in n-hexane, and dropping the mixture into methanol twice. The product was dried at a reduced pressure for one night and day at 60° C. to thereby obtain a homopolymer 1.

Comparative Example 3

To a reaction apparatus equipped with a reflux condenser and capable of stirring, 25.6 g of methoxymonoethylene glycol acrylate (MMEGA) (made by TOKYO CHEMICAL INDUSTRY CO., LTD.), 0.0246 g of azobisisobutyronitrile (AIBN) (made by Wako Pure Chemical Industries, Ltd.), and 119.1 g of dimethylacetamide (made by Kishida Chemical CO., LTD.) were added, and a polymerization reaction was performed at 80° C. for 20 hours. The obtained polymer solution was dropped into n-hexane under stirring using a Pasteur pipette, and a crude polymer was obtained. 2 g of the obtained crude polymer was dissolved in 2 g of tetrahydrofuran and dropped into 20 g of a poor solvent (n-hexane) under stirring using a Pasteur pipette. The operation of recovering the precipitate by decantation, adding the same weight of tetrahydrofuran for dissolution, and dropping the mixture into the poor solvent was repeated twice, thereafter performing drying at reduced pressure for 4 days under the condition of a reduced pressure at 0.1 Torr at 60° C. to thereby obtain a homopolymer 2.

Example 2

33.3 g of methoxytriethylene glycol acrylate (hereinafter, it will be abbreviated as MTEGA) (made by SHIN-NAKAMURA CHEMICAL CO., LTD.), 50.7 g of 2-ethylhexyl acrylate (hereinafter, it will be abbreviated as EHA) (made by TOKYO CHEMICAL INDUSTRY CO., LTD.), 0.0815 g of azobisisobutyronitrile (AIBN) (made by Wako Pure Chemical Industries, Ltd.), and 33.7 g of ethanol (made by Wako Pure Chemical Industries, Ltd.) were added, and a polymerization reaction was performed under the condition of 80° C. for 20 hours. After completion of the polymerization reaction, a polymerization solvent was removed by evaporation for 4 days under the conditions of 60° C. and 1 Torr, and a crude (meth)acrylate copolymer was obtained. 2 g of the obtained crude (meth)acrylate copolymer was dissolved in 2 g of tetrahydrofuran and dropped into 20 g of a poor solvent (weight ratio of methanol/water was set to 85/15) under stirring using a Pasteur pipette. The precipitate was recovered by decantation, and re-precipitation purification by the similar operation was repeated twice, thereafter performing drying at reduced pressure for 4 days under the condition of a reduced pressure at 0.1 Torr at 60° C. to thereby obtain a copolymer 3.

Example 3

33.3 g of methoxytriethylene glycol acrylate (hereinafter, it will be abbreviated as MTEGA) (made by SHIN-NAKA- MURA CHEMICAL CO., LTD.), 50.7 g of 2-ethylhexyl acrylate (hereinafter, it will be abbreviated as EHA) (made by TOKYO CHEMICAL INDUSTRY CO., LTD.), 0.0654 g of azobisisobutyronitrile (AIBN) (made by Wako Pure Chemical Industries, Ltd.), and 126 g of ethanol (made by Wako Pure Chemical Industries, Ltd.) were added, and a polymerization reaction was performed under the condition of 80° C. for 20 hours. After completion of the polymerization reaction, a polymerization solvent was removed by evaporation for 4 days under the conditions of 60° C. and 1 Torr, and a crude (meth)acrylate copolymer was obtained. 2 g of the obtained crude (meth)acrylate copolymer was dissolved in 2 g of tetrahydrofuran and dropped into 20 g of a poor solvent (weight ratio of methanol/water was set to 85/15) under stirring using a Pasteur pipette. The precipitate was recovered by decantation, and re-precipitation purification by the similar operation was repeated twice, thereafter performing drying at reduced pressure for 4 days under the condition of a reduced pressure at 0.1 Torr at 60° C. to thereby obtain a copolymer 4.

Example 4

33.4 g of methoxytriethylene glycol acrylate (hereinafter, it will be abbreviated as MTEGA) (made by SHIN-NAKAMURA CHEMICAL CO., LTD.), 38.9 g of lauryl acrylate (hereinafter, it will be abbreviated as LA) (made by TOKYO CHEMICAL INDUSTRY CO., LTD.), 0.0747 g of azobisisobutyronitrile (AIBN) (made by Wako Pure Chemical Industries, Ltd.), and 72.5 g of ethyl acetate (made by TOKYO CHEMICAL INDUSTRY CO., Ltd.) were added, and a polymerization reaction was performed under the condition of 80° C. for 20 hours. After completion of the polymerization reaction, a polymerization solvent was removed by evaporation for 4 days under the conditions of 60° C. and 1 Torr, and a crude (meth)acrylate copolymer was obtained. 2 g of the obtained crude (meth)acrylate copolymer was dissolved in 2 g of tetrahydrofuran and dropped into 20 g of a poor solvent (weight ratio of methanol/water was set to 85/15) under stirring using a Pasteur pipette. The precipitate was recovered by decantation, and re-precipitation purification by the similar operation was repeated twice, thereafter performing drying at reduced pressure for 4 days under the condition of a reduced pressure at 0.1 Torr at 60° C. to thereby obtain a copolymer 5.

2. Measurement of Physical Property and Structure of the Polymer (1) Measurement of Number-Average Molecular Weight 3 mL of a transfer phase for GPC measurement was added to each of the copolymers 1 to 5 or each of the homopolymers 1 and 2 (15 mg), then these samples were dissolved and filtration was performed with 0.45 μm of a hydrophilic PTFE (Millex-LH, made by Millipore Japan Co.). Measuring apparatuses of a 510 high pressure pump, a 717 plus automatic injection device (made by Nihon Waters K.K.), and RI-101 (made by Showa Denko K.K.) were used for the GPC measurement, and PLgel 5μ MIXED-D (600×7.5 mm) (made by Polymer Laboratories, Ltd.) was used for a column, and the measurement was performed at a normal column temperature, and tetrahydrofuran (THF) added with 0.03% by weight of dibutyl hydroxy toluene (BHT) was used as the transfer phase. Detection was performed at RI, and 50 μL of the test sample solution was injected. Molecular weight calibration was performed by single dispersion PMMA (Easi Cal: made by Polymer Laboratories, Ltd.).

(2) Measurement of a Polymer Composition Ratio

Each of the copolymers 1 to 5 or each of the homopolymers 1 and 2 (50 mg) was respectively added to a NMR test tube (speculation: N-5, made by Nihon Seimitsu Kagaku Co., Ltd.) with a Pasteur pipette, and then, 0.7 mL of chloroform-d (made by Wako Pure Chemical Industries, Ltd.) was added thereto to be sufficiently blended, and the test tube was covered with a cap for the sample (speculation: NC-5, made by Nihon Seimitsu Kagaku Co., Ltd.). A copolymer composition ratio was calculated by carrying out 1H NMR measurement under room temperature using GEMINI-200 made by VARIAN Co. The copolymer composition ratio was determined using the integral ratio of proton derived from terminal methyl group of alkyl (meth)acrylate and the integral ratio of proton derived from terminal methoxy group of polyethylene glycol (meth)acrylate.

(3) Calculation of a Yield

Ratio of the polymer, after re-precipitation and drying, to the total weight of the charged monomer for the polymer was calculated as a yield. When the yield was within a range of 50 to 90%, it was evaluated as good.

(4) Measurement of Residual Amount of Unreacted Monomer

Each of the copolymers 1 to 5 or each of the homopolymers 1 and 2 (50 mg) was respectively added to a NMR test tube (speculation: N-5, made by Nihon Seimitsu Kagaku Co., Ltd.) with a Pasteur pipette, and then, 0.7 mL of chloroform-d (made by Wako Pure Chemical Industries, Ltd.) was added thereto to be sufficiently blended, and the test tube was covered with a cap for the sample (speculation: NC-5, made by Nihon Seimitsu Kagaku Co., Ltd.). A copolymer composition ratio was calculated by carrying out $^1$H NMR measurement under room temperature using GEMINI-200 made by VARIAN Co. For the calculation, the operator of $[M1/(P1+M1)] \times 100$ using an integral ratio of proton existing in double bond (M1) derived from the unreacted monomer and the sum of integral ratios of proton (P1) derived from alkyl (meth)acrylate and methoxy polyethylene glycol in the polymer was used. When the monomer content was not more than 5% by mol, it was evaluated as good.

(5) Alcohol-Solubility Test

Each of the copolymers 1 to 5 or each of the homopolymers 1 and 2 (500 mg) was added to a 50 mL-vial, and 2 mL of ethanol was then added and the sample was allowed to stand at room temperature for 48 hours. Then, dissolution was visually confirmed.

(6) Measurement of a Glass Transition Temperature

A differential scanning calorimeter (DSC-50, made by SHIMADZU CORPORATION) was used. Each of the copolymers 1 to 5 or each of the homopolymers 1 and 2 (10 mg) was packed in a cell (Al cell, 6 mmp, made by SHIMADZU CORPORATION) and covered with a lid, and crimped and sealed with a sealer crimper (made by SHIMADZU CORPORATION), and then, the sample was set in a measuring apparatus to be measured. The sample was heated from 30° C. to 300° C. at a rising rate of 50° C. per minute, kept for 5 minutes, cooled down to −100° C. at 10° C./minute and kept for 5 minutes. Glass transition temperature (Tg) was calculated from the thermal hysteresis from −100° C. to 300° C. thereafter.

3. Property Test of the Polymer (1) Sample Preparation for the Platelet Adhesion test—Aging Treatment 19.8 g of ethanol was added to each of the copolymers 1 to 5 or each of the homopolymers 1 and 2 (0.2 g) and then the sample was dissolved, thereby preparing 1% by weight of an ethanol solution to obtain a treating liquid. Plasticized PVC sheet with a size of 25×25×1 mm was immersed in each treating liquid, and then the plasticized PVC sheet was taken out and dried at 60° C. for 24 hours. Further, aging was performed for 30 days in physiological saline at 37° C. to form an aging sample for a blood compatibility test. Regarding the samples after 30 days-aging, a weight reduction ratio was measured. Samples having a weight reduction ratio of 20% by weight or less were evaluated as good, and samples having a weight reduction ratio of more than 20% by weight were evaluated as poor. It can be determined that the samples were significantly dissolved in physiological saline in the case of 20% or more of weight reduction even if considering a measurement error.

(2) Platelet Adhesion Test 60 mL of citrated fresh blood removed from a rabbit was equally divided in two 50 mL-centrifuge tubes, and centrifuged at 1000 rpm for 10 minutes. The supernatants thereof were equally divided in four 10 mL-centrifuge tubes. The supernatants were further centrifuged at 1500 rpm for 10 minutes, and the supernatants were then removed to separate platelet pellets that were a precipitate. Thereto was added HBSS (Hanks' balanced salt solution) for dilution to thereby obtain a platelet solution having a platelet concentration of $3.0 \times 10^8$/mL. The platelet concentration was confirmed with a blood cell counter (KX-21, made by SYSMEX CORPORATION). The platelet solution having this concentration was used as a test liquid. 0.2 mL of the obtained test liquid was taken and dropped on the upper surface of the above-mentioned sample in a 60×15 mm petri dish (made of polystyrene, made by Corning Inc.), thereafter covered with a lid and incubated at 37° C. for 1 hour. Then, 5 mL of an aqueous solution containing 2.5% by weight of glutaric aldehyde was added thereto and the mixture was stood still at room temperature for 24 hours. An operation of replacing the solution in the petri dish with water was performed three times, and water was then discharged therefrom. The PVC sheet washed with water was frozen at −5° C. for 24 hours, and then dried at 0.1 Torr for 24 hours. A piece with a size of 10×10 mm was cut out from a region of the PVC sheet on which the platelet solution was dropped, and adhered to a sample table for a scanning electron microscope (SEM) with a double sided tape to be used as a measurement sample. Conditions of adhered platelets were photographed by SEM using the sample having been subjected to ion vapor deposition. The SEM photos (×3000 times) taken were visually observed for comparison. When the attached platelet number was 50 or less, the sample was evaluated to be good, because it can be considered that the platelets do not significantly adhere even if considering the distribution of the platelets over the photographed region. And when the attached platelet number was more than 50, the sample was evaluated to be defective.

(3) Measurement test of Complement—Complement Value (Complement Evaluation—Sample Preparation)

A solution obtained by adding 19.8 g of ethanol to each of the copolymers 1 to 5 or each of the homopolymers 1 and 2 (0.2 g) and dissolving the sample was used as a treating liquid, and 1 g of glass beads with a diameter of 1 mm was immersed in each treating liquid for 10 seconds, the liquid was discharged therefrom, and then the glass beads were dried at 60° C. for 24 hours. Further, the glass beads were subjected to aging in water at 37° C. for 30 days, and then dried to prepare a sample for complement (complement value and C3a) evaluation.

(Measurement of Complement—Complement Value)

10 mL of human fresh blood separated in a 50 mL-centrifuge tube made of polypropylene (made by IWAKI Co., Ltd.) was coagulated by standing still at room temperature and centrifuged at 3000 rpm for 30 minutes (LC06, made by TOMY SEIKO Co., Ltd.) to thereby obtain 3.5 mL of serum. 0.1 mL of a diluted liquid was added to 1 g of glass beads with a diameter of 1 mm that had been subjected to a surface-treatment by each of the copolymers 1 to 5 or each of the homopolymers 1 and 2, and then incubated at 37° C. for 1 hour. 0.2 mL of the obtained serum was added thereto and incubated at 37° C. for 1 hour in the same manner. 2.6 mL of the diluted liquid, 12.5 µL of serum in contact, and 0.4 mL of sensitized sheep erythrocytes were sufficiently mixed, and then incubated at 37° C. for 1 hour, cooled at 0° C. for 10 minutes, and then centrifuged at 2000 rpm, and an absorbance of 2 mL of the supernatant was measured at 541 nm (U-2000 Spectrometer, made by HITACHI, Ltd.). At the same time, a mixture of 2.6 mL of a diluted liquid and 0.4 mL of sensitized sheep erythrocytes was considered as a liquid without hemolysis and data thereof was deducted. Auto CH50-L "Seiken" (universal product No. 400437, 52 mL of diluted liquid, 6 mL of sensitized sheep erythrocytes) was used for measurement. A relative absorbance was calculated based on an absorbance of a glass beads that had not been subjected to a surface treatment as 1. 1.2 or more was determined to be good. In the case of less than 1.2, it can be determined that a complement was significantly activated even if considering a measurement error.

(Measurement of Complement—C3a)

10 mL of human fresh blood separated in a 50 mL-centrifuge tube made of polypropylene (made by IWAKI Co., Ltd.) and 1 mL of an aqueous solution containing 3.2% by weight of trisodium citrate were sufficiently mixed, and then centrifuged at 2000 rpm for 30 minutes (LC06, made by TOMY SEIKO Co., Ltd.) to thereby obtain 4.5 mL of plasma. 0.5 mL of physiological saline was added to 4.6 g of glass beads with a diameter of 1 mm that had been subjected to a surface-treatment with each of the copolymers 1 to 5 or each of the homopolymers 1 and 2 by the above described method, and then incubated at 37° C. for 1 hour, thereto was added 1 mL of the obtained plasma, incubation was performed at 37° C. for 1 hour in the same manner, and 0.5 mL of the liquid was used as an evaluation sample. The sample was rapidly cooled to −20° C. or lower and stored until measurement. The evaluation was performed by using Human Complement C3a Des Arg[125I] Biotrak Assay System, code RPA518 (made by Amersham Biosciences, Corp.) according to an attached manual. The evaluation value was calculated as an average value of the three data, and since a value of an untreated evaluation sample was 94 ng/mL, it was considered that when the C3a value was 100 ng/mL or more, the complement was significantly activated even if considering a measurement error, and thus, the value was evaluated to be defective.

Results of measurements in the following Examples 1 to 4 and Comparative Examples 1 to 3 are listed in Table 1. It is noted that the property of the copolymer of the present invention satisfies the essential features as an oxygenator.

TABLE 1

|  | Example 1 | Comparative Example 1 | Comparative Example 2 | Comparative Example 3 | Example 2 | Example 3 | Example 4 |
|---|---|---|---|---|---|---|---|
| Hydrophobic (meth)acrylate | EHA | EA | EHA | — | EHA | EHA | LA |
| Number of carbon atoms in $R_1$ | 8 | 2 | 8 | — | 8 | 8 | 12 |
| Hydrophilic (meth)acrylate | MTEGA | MPEGA | — | MMEGA | MTEGA | MTEGA | MTEGA |
| N number | 3 | 9 | — | 1 | 3 | 3 | 3 |
| Ratio of hydrophobic (meth)acrylate/ hydrophilic (meth)acrylate | 67.5/32.5 | 15.7/84.3 | 100/0 | — | 67.5/32.5 | 69.2/30.8 | 56.4/43.6 |
| Solubility to alcohols | ○ | ○ | ○ | ○ | ○ | ○ | ○ |
| Water-insolubility | ○ | x | ○ | ○ | ○ | ○ | ○ |
| Glass transition temperature (° C.) | −65 | −70 | −57 | −36 | −63 | −61 | −42 |
| Aging treatment | ○ | x | ○ | ○ | ○ | ○ | ○ |
| Platelet adhesion test | good | defective | defective | good | good | good | good |
| Number-average molecular weight | 14,600 | 15,000 | 20,000 | 11,000 | 19,700 | 9,700 | 14,200 |
| Evaluation of complement value | 1.44 | 0.98 | 1.32 | 0.94 | 1.41 | 1.30 | 1.26 |
| Determination | good | defective | good | defective | good | good | good |
| Evaluation of C3a | 81 | 102 | 98 | 114 | 85 | 93 | 74 |
| Determination | good | defective | good | defective | good | good | good |

4. Manufacture of an Oxygenator and Property Test of the Same (1) Manufacture of an Oxygenator About 2,000 hollow fiber membranes made of porous polypropylene where inner diameter was 195 μm, outer diameter was 295 μm and vacancy factor was about 35% were received in a housing to prepare an oxygenator of hollow fiber membrane of an external perfusion type where membrane area was 1.8 m². Each of the treating liquids mentioned later was charged in the outer area of the hollow fiber membrane of the oxygenator, the liquid was discharged therefrom, then nitrogen gas was sent with the pressure of about 1 kgf/cm² from the blood inlet side and the mixed solvent of water and ethanol was removed to manufacture an oxygenator.

(2) Preparation of the Treating Liquids

Examples and Comparative Examples for preparing the treating liquids using the (co)polymers manufactured in the above Examples 1 to 4 an Comparative Examples 1 to 3 are shown below.

Example 5

The copolymer 1 (0.6 g) of Example 1 was dissolved in 36.9 g of ethanol followed by adding to and mixing with 262.5 g of water whereupon a treating liquid was prepared according to the operation of Example 1. Said treating liquid was in such a state where the copolymer was dispersed in the mixed liquid or, in other words, the so-called suspension. This was named a treating liquid 1.

Example 6

The copolymer 1 (0.6 g) of Example 1 was dissolved in 299.4 g of ethanol to prepare a treating liquid in accordance with the operation of Example 1. This was named a treating liquid 2. Since the solvent was a single organic solvent in that case, the copolymer was homogeneously dissolved resulting in a state of solution. Possibly due to the above, some infiltration of the treating liquid was noted even in the side which did not contact the blood when the oxygenator was treated with said treating liquid.

Comparative Example 4

The copolymer 2 (0.6 g) of Comparative Example 1 was dissolved in 299.4 g of ethanol to prepare a mixed solution in accordance with the operation of Example 1. This was named a treating liquid 3. Since the solvent was a single organic solvent in that case, the copolymer was homogeneously dissolved resulting in a state of solution. Possibly due to the above, some infiltration of the treating liquid was noted even in the side which did not contact the blood when the oxygenator was treated with said treating liquid.

Comparative Example 5

The homopolymer 1 (0.6 g) of Comparative Example 2 was dissolved in 299.4 g of ethanol to prepare a mixed solution in accordance with the operation of Example 1. This was named a treating liquid 4. Since the solvent was a single organic solvent in that case, the polymer was homogeneously dissolved resulting in a state of solution. Possibly due to the above, some infiltration of the treating liquid was noted even in the side which did not contact the blood when the oxygenator was treated with said treating liquid.

Comparative Example 6

The homopolymer 2 (0.6 g) of Comparative Example 3 was dissolved in a mixed solvent (water/ethanol/methanol=179.7 g/89.8 g/29.9 g) to prepare a mixed solution in accordance with the operation of Example 1. This was named a treating liquid 5. Since the solvent was a single organic solvent in that case, the polymer was homogeneously dissolved resulting in a state of solution. Possibly due to the above, some infiltration of the treating liquid was noted even in the side which did not contact the blood when the oxygenator was treated with said treating liquid.

Comparative Example 7

The copolymer 2 (0.6 g) of Comparative Example 1 was dissolved in 299.4 g of methanol to prepare a mixed solution in accordance with the operation of Example 1. This was named a treating liquid 6. Since the solvent was a single organic solvent in that case, the polymer was homogeneously dissolved resulting in a state of solution. Possibly due to the above, some infiltration of the treating liquid was noted even in the side which did not contact the blood when the oxygenator was treated with said treating liquid.

Example 7

The copolymer 3 (0.6 g) of Example 2 was dissolved in 36.9 g of ethanol followed by adding to and mixing with 262.5 g of water whereupon a treating liquid was prepared according to the operation of Example 1. Said treating liquid was in such a state where the copolymer was dispersed in the mixed liquid or, in other words, the so-called suspension. This was named a treating liquid 7.

Example 8

The copolymer 4 (0.6 g) of Example 3 was dissolved in 36.9 g of ethanol followed by adding to and mixing with 262.5 g of water whereupon a treating liquid was prepared according to the operation of Example 1. Said treating liquid was in such a state where the copolymer was dispersed in the mixed liquid or, in other words, the so-called suspension. This was named a treating liquid 8.

Example 9

The copolymer 5 (0.6 g) of Example 4 was dissolved in 36.9 g of ethanol followed by adding to and mixing with 262.5 g of water whereupon a treating liquid was prepared according to the operation of Example 1. Said treating liquid was in such a state where the copolymer was dispersed in the mixed liquid or, in other words, the so-called suspension. This was named a treating liquid 9.

(3) Property Test (Evaluation of Complement of Coating Hollow Fiber Membrane)

10 mL of human fresh blood separated in a 50 mL-centrifuge tube made of polypropylene (made by IWAKI Co., Ltd.) was coagulated by standing still at room temperature and centrifuged at 3000 rpm for 30 minutes (LC06, made by TOMY SEIKO Co., Ltd.) to thereby obtain 3.5 mL of serum. Hollow fiber membrane (0.02 g; length: 1.5 cm) made of PP for an oxygenator was dipped for 10 seconds in each of the above-mentioned treating liquids and dried at 60° C. for 3 hours. After that, the inner surface of a 10-mL spitz made of PP was subjected to a surface treatment similarly, dried and further subjected to a surface treatment and the resulting hollow fiber and spitz were aged in water at 37° C. for 30 days and dried to give a sample for evaluation. Coated hollow fiber membrane was placed in said surface-treated spitz followed by sealing to prepare a sample. To the sample was added 0.1 mL of a diluted liquid, and then incubated at 37° C. for 1 hour. 0.2 mL of the obtained serum was added thereto and incubated at 37° C. for 1 hour in the same manner. 2.6 mL of the diluted liquid, 12.5 μL of serum in contact, and 0.4 mL of sensitized sheep erythrocytes were sufficiently mixed, and then incubated at 37° C. for 1 hour, cooled at 0° C. for 10 minutes, and then centrifuged at 2000 rpm, and an absorbance of 2 mL of the supernatant was measured at 541 nm (U-2000 Spectrometer, made by HITACHI, Ltd.). At the same time, a mixture of 2.6 mL of a diluted liquid and 0.4 mL of sensitized sheep erythrocytes was considered as a liquid without hemolysis and data thereof was deducted. Auto CH50-L "Seiken" (universal product No. 400-437, 52 mL of diluted liquid, 6 mL of sensitized sheep erythrocytes) was used for measurement. A relative absorbance was calculated based on an absorbance of a glass beads that had not been subjected to a surface treatment as 1. 1.2 or more was determined to be good while, less than 1.2 was determined to be defective. In the case of less than 1.2, it can be determined that a complement was significantly activated even if considering a measurement error.

(Fibrin Gel Formation Experiment)

45 mL of citrated bovine blood in a 50 mL-centrifuge tube made of polypropylene (made by IWAKI Co., Ltd.) was centrifuged at 2000 rpm for 30 minutes (LC06, made by TOMY SEIKO Co., Ltd.) to thereby obtain 8 mL of bovine blood plasma. 1 g of glass beads with a diameter of 1 mm subjected to a surface treatment by the above described method and the 10 mL-centrifuge tube made of polystyrene that had been surface-treated in the interior surface in the same manner were subjected to aging in water at 37° C. for 30 days, and then dried to be used as evaluation samples. 1.8 mL of bovine plasma was added to the centrifuge tube in which said glass beads after the surface treatment are sealed, and then incubated at 37° C. for 3 minutes, 0.2 mL of an aqueous solution with 0.125 N of $CaCl_2$ was added thereto and mixed, and the time immediately after the mixing was considered to be reaction initiation and the mixture was incubated at 37° C. Presence or absence of completion of gelation was confirmed at an interval of 10 seconds after the reaction initiation, and a gelation time was measured. The N number was assumed to be 3, and an average value thereof was calculated. Since a coagulation time of a surface-untreated sample was 635 seconds, the case of less than 600 seconds where it can be determined that the coagulation system is significantly activated even if considering a measurement error was evaluated to be good. Further, a protein concentration in the bovine blood plasma used in the experiment was calculated by a weighing amount after freeze drying and found to be 82 mg/mL.

(Coating to an Oxygenator and Confirmation of Permeability of the Hollow Fiber)

About 20,000 porous polypropylene hollow fiber membranes where inner diameter was 195 μm, outer diameter was 295 μm and vacancy factor was about 35% were received in a housing to prepare a hollow fiber membrane oxygenator of an external blood perfusion type having a membrane area of 1.8 $m^2$. Each of the treating liquid 1 to 9 was charged in the outer side of the hollow fiber membrane of the oxygenator, the liquid was discharged therefrom, nitrogen gas was flown from the blood inlet side at the pressure of 1 $kgf/cm^2$ and it was confirmed by naked eye whether the treating liquid was flown out from the gas permeation side within 10 minutes. When the treating liquid was not leaked out, it was judged that leakage of the plasma due to making the hollow fiber membrane into hydrophilic and lowering of gas permeability due to clogging of pores were able to be suppressed to the maximum extent. Oxygenators 1 to 9 were prepared by said method.

(Aging Treatment of an Oxygenator)

Water was charge in each of the oxygenators 1 to 9, subjected to aging at 37° C. for 7 days and dried to give oxygenators 10 to 18.

(4) Elution Test (Extraction)

Distilled water of 80° C. was charged in the polymer-covered side of each oxygenator followed by being allowed to stand at 70° C. for 30 minutes and then 250 mL of extract was recovered and used as a test liquid in the following elution test. Distilled water which was allowed to stand at 70° C. for 30 minutes was used as a blank test liquid.

(pH)

Electric source of a pH meter was made on and the electrodes were washed with distilled water for injection and wiped with Kim Wipe. A standard liquid of pH 7 was set and electric magnetic rods were rotated using a stirrer to conduct calibration. A standard liquid of pH 4 was calibrated similarly. A test liquid (20 mL) was collected to a glass bottle for measurement using a hole pipette. A potassium chloride solution was collected using a 1-mL hole pipette into a glass bottle for the measurement in which a test liquid was placed and a stirrer chip was placed there. A test liquid was set and then the stirrer was rotated. The pH was determined using the following formula.

$$pH = pH(\text{test liquid}) - pH(\text{blank test liquid})$$

When the absolute value of the changes in pH was less than 0.2, exposure of acrylic acid structure due to hydrolysis, etc. of the acrylate side chain was judged to be slight whereby it was evaluated as good while the case where it was not less than 0.2 was evaluated as defective.

(Reducing Substance)

Slidax was connected to an electric heater and a socket was connected thereto. The electric heater was set at 600 W with a Slidax at 40 V and a pre-heating was conducted for 1 hour. A test liquid (10 mL) was collected into a 100-mL Erlenmeyer flask with a ground stopper using a hole pipette. A 1/100 N solution of potassium permanganate (20 mL) was added to the Erlenmeyer flask. A 10% diluted sulfuric acid (1 mL) was added to the Erlenmeyer flask. A ground stopper was applied followed by shaking to homogeneously mix. Bubble stones were placed and set in the 100-mL Erlenmeyer flask followed by boiling for 15 minutes. After start of boiling, the boiling was further conducted for 3 minutes. The flask was taken out, a ground stopper was applied by sandwiching with a package paper and cooling was conducted for 5 minutes using a cooler exclusively therefor. A solution of 100 g/L of potassium iodide (1 mL) was added thereto, a ground stopper was applied thereto and shaking was conducted to mix followed by being allowed to stand for 10 minutes. Five drops of a starch indicator was added thereto directly from a dropping bottle followed by shaking to mix. Titration was carried out by adding a 1/100N solution of sodium thiosulfate and the stage where dark blue color completely disappeared was adopted as an end point. The same measurement was also conducted where the test liquid was substituted with a blank test liquid. Amount of the reducing substance in the test liquid was calculated by the following formula.

$$\text{Amount of the reducing substance (ml)} = \text{Titer of the test liquid (ml)} - \text{Titer of the blank test liquid (ml)}$$

When the amount of the reducing substance was not more than 0.8 mL, the polymer structure was said to be stably present whereby it was evaluated to be good while the case when it was more than 0.8 mL was evaluated to be defective.

(Residue after Evaporation)

Fifty-mL beakers were dried at 105° C. for 2 hours using a drying machine for utensils. Tweezers were disinfected using 70% ethanol, the beakers were taken out from the drying machine for utensils and allowed to stand and cool for 20 minutes in a desiccator. The bakers were taken out from the desiccator and each of them was weighed precisely. A test liquid (20 mL) was collected in a precisely-weighed 50-mL beaker and dried at 105° C. for 60 minutes and the beaker was allowed to cool for 20 minutes in the desiccator. The beaker was taken out from the desiccator and precisely weighed and the weight was deducted from the blank beaker weight to give the amount of the residue after evaporation. When said amount of the residue after evaporation was not more than 10 mg, elution into the blood was judged to be well suppressed whereby it was evaluated as good while the case where it was more than 10 mg was evaluated as defective.

(Atomic Absorption Measurement)

The measurement was conducted using a Shimadzu Atomic Absorption/Flame Spectrophotometer AA-670 (made by SHIMADZU CORPORATION). A 1000 ppm standard liquid was diluted. Adjustment of concentration of calibration curve was conducted with zinc (0.2 ppm, 0.5 ppm, 1.0 ppm), lead (0.5 ppm, 1.0 ppm, 2.0 ppm) and cadmium (0.05 ppm, 0.1 ppm, 0.2 ppm). After the calibration curve was prepared, quantification of concentration in the test liquid was conducted. When zinc concentration, lead concentration and cadmium concentration were not more than 0.8 ppm, 0.4 ppm and 0.04 ppm, respectively, danger to organisms was able to be avoided whereby such a case was evaluated as good while the case where each was more than the stipulated value was evaluated as defective.

(Test for Cleanliness)

A test liquid (10 mL) was weighed and taken out using a graduated cylinder. Filter papers (white and green) were placed on a filter, a filter device was placed thereon and fixed with a cramp and the test liquid was filtered. The filter papers were taken out from the filtering device, placed on a Petri dish and covered. A blank test was also conducted similarly. Numbers of foreign bodies on the filter paper after filtration were counted using a magnifying glass (made by Olympus) and calculated by the following formula.

$$\text{Foreign body numbers} = (\text{Counted numbers})/(10 \text{ (mL)}/250 \text{ (mL)})\times \frac{1}{2}$$

Since the risk of contamination of foreign bodies was able to be avoided when the foreign body numbers were not more than 20, it was evaluated as good while the case where it was more than 20 was evaluated as defective. When they were not more than 20, it was judged to be suitable.

(Foaming)

The extract (5 mL) was collected in a test tube and a ground stopper was applied. The test tube equipped with a ground stopper was vigorously shaken up and down for five times within one second and then said test tube was allowed to stand on a test tube stand. State of foams after 2 minutes from the stage where the shaking was stopped was evaluated according to the following criteria. Thus, A: foams formed a layer throughout all areas; B: foams were present in a ring form; C: presence of foams was not throughout the whole circumference and foam numbers were 10 or more; D: although foams were present, their numbers were less than 10; E: no foam was present at all. With regard to D and E where foams were less than 10 after 2 minutes, they were able to be judged that there was no eluting component whereby such cases were evaluated to be good and A to C where foam numbers were 10 or more were evaluated to be defective.

(Absorbance)

Absorbance at 220 nm was measured using water as a blank. When the absorbance was not more than 0.2, it was able to be judged that, even when extraction error was taken into consideration, there was no eluting component whereby it was evaluated as good while the case when it was more than 0.2 was evaluated as defective.

(5) Plasma Leakage Test

The oxygenator as shown in each of Examples and Comparative Examples was incorporated into the extracorporeal circulation circuit, 1100 mL of bovine blood to which citric acid was added and 1900 mL of Ringer's solution to which lactic acid was added were charged, perfusion of 1 L per minute was conducted at 37° C. for 8 hours and confirmation by naked eye was conducted to check whether the leakage of plasma was noted.

Main results concerning the main property of the above oxygenator are shown in Table 2.

TABLE 2

| | Example 5 | Example 6 | Comparative Example 4 | Comparative Example 5 | Comparative Example 6 | Comparative Example 7 | Example 7 | Example 8 | Example 9 |
|---|---|---|---|---|---|---|---|---|---|
| Fibrin gel formation experiment | 830 sec. good | 840 sec. good | 590 sec. defective | 540 sec. defective | 420 sec. defective | 410 sec. defective | 850 sec. good | 830 sec. good | 830 sec. good |
| Permeability of the hollow fiber | absent | present | present | present | absent | present | absent | absent | absent |
| Platelet adhesion test | good | good | defective | defective | good | good | good | good | good |
| Complement test of the hollow fiber | 1.28 good | 1.31 good | 0.97 defective | 1.21 good | 1.00 defective | 1.00 defective | 1.24 good | 1.29 good | 1.31 good |
| pH | −0.156 good | −0.142 good | −0.098 good | −0.126 good | −0.286 defective | −0.296 defective | −0.136 good | −0.153 good | −0.147 good |
| Reducing substance (mL) | 0 good | 0 good | 0 good | 0 good | 0.1 good | 0.2 good | 0 good | 0 good | 0 good |
| Residue after evaporation (mg) | 1.0 good | 1.1 good | 0.3 good | 10.7 good | 0.8 good | 0.9 good | 0.5 good | 1.1 good | 0.8 good |
| Zinc (ppm) | undetected good | undetected good | undetected good | undetected good | undetected good | undetected good | undetected good | undetected good | undetected good |
| Lead (ppm) | 0.127 good | 0.132 good | 0.119 good | 0.124 good | 0.134 good | 0.122 good | 0.131 good | 0.120 good | 0.118 good |
| Cadmium (ppm) | 0.003 good | 0.002 good | 0.001 good | 0.001 good | 0.004 good | 0.004 good | 0.002 good | 0.003 good | 0.003 good |
| Cleanliness (counts) | 0 good | 0 good | 0 good | 0 good | 0 good | 0 good | 0 good | 0 good | 0 good |
| Foaming | D good | D good | D good | D good | D good | D good | D good | D good | D good |
| Absorbance (220 nm) | 0.013 good | 0.016 good | 0.009 good | 0.011 good | 0.014 good | 0.014 good | 0.012 good | 0.009 good | 0.013 good |
| Plasma leakage test | no leakage | no leakage | no leakage | no leakage | no leakage | no leakage | no leakage | no leakage | no leakage |

INDUSTRIAL APPLICABILITY

The oxygenator of a hollow fiber membrane type in accordance with the present invention is surely becoming as an auxiliary function for respiration being widely used together with the establishment of surgical heart operation. It is of course expected to play a role as a continuous auxiliary function when recovery of the surgical heart operation is delayed. Further, it is able to be used in the medical field where function of respiratory organ as a whole is demanded such as relief, support, etc. of patients suffering from respiratory insufficiency, patients dealing with the lowering of pulmonary functions and chronic patients where lung or pulmonary function is demanded. Still further, the oxygenator in accordance with the present invention greatly contributes in utilization, role and development of artificial organs and in growth of medical materials in the medical fields as a whole.

The invention claimed is:

1. An oxygenator comprising a plurality of hollow fiber membranes positioned in a housing, wherein at least a part of the hollow fiber membranes to contact blood during use is coated with a (meth)acrylate copolymer formed by the copolymerization of a hydrophobic (meth)acrylate with a hydrophilic (meth)acrylate at a molar ratio of (50 to 90):(50 to 10), wherein the (meth)acrylate copolymer is water-insoluble to the extent that when 1% by weight of the (meth)acrylate copolymer is allowed to stand for 30 days in 99% by weight of a physiological saline solution of 37° C., the (meth)acrylate copolymer is not reduced in weight by more than 1%.

2. The oxygenator of claim 1, wherein the hydrophobic (meth)acrylate contains alkyl (meth)acrylate represented by formula 1:

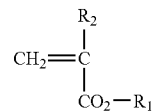

[1]

wherein $R_1$ represents an alkyl group or aralkyl group having 6 to 18 carbon atoms, and $R_2$ represents a hydrogen atom or a methyl group.

3. The oxygenator of claim 1, wherein the hydrophilic (meth)acrylate contains methoxy polyethylene glycol (meth)acrylate represented by formula 2:

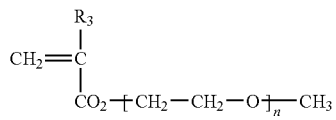

[2]

wherein $R_3$ represents a hydrogen atom or a methyl group, and n represents 2 to 1,000.

4. The oxygenator of claim 1, wherein the oxygenator is an internal perfusion type oxygenator in which the inner surface of the hollow fiber membranes to contact blood during use is coated with the (meth)acrylate copolymer.

5. The oxygenator of claim 1, wherein the oxygenator is an external perfusion type oxygenator in which the outer surface of the hollow fiber membranes to contact blood during use is coated with the (meth)acrylate copolymer.

6. The oxygenator of claim 1, wherein the number-average molecular weight of the (meth)acrylate copolymer comprising the hydrophobic (meth)acrylate and the hydrophilic (meth)acrylate is from 2,000 to 200,000.

7. The oxygenator of claim 2, wherein the number-average molecular weight of the (meth)acrylate copolymer comprising the hydrophobic (meth)acrylate and the hydrophilic (meth)acrylate is from 2,000 to 200,000.

8. The oxygenator of claim 3, wherein the number-average molecular weight of the (meth)acrylate copolymer comprising the hydrophobic (meth)acrylate and the hydrophilic (meth)acrylate is from 2,000 to 200,000.

9. The oxygenator of claim 4, wherein the number-average molecular weight of the (meth)acrylate copolymer comprising the hydrophobic (meth)acrylate and the hydrophilic (meth)acrylate is from 2,000 to 200,000.

10. The oxygenator of claim 5, wherein the number-average molecular weight of the (meth)acrylate copolymer comprising the hydrophobic (meth)acrylate and the hydrophilic (meth)acrylate is from 2,000 to 200,000.

11. The oxygenator of claim 2, wherein the hydrophilic (meth)acrylate contains methoxy polyethylene glycol (meth)acrylate represented by formula 2:

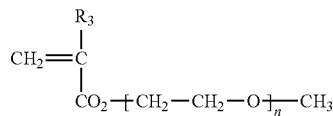

[2]

wherein $R_3$ represents a hydrogen atom or a methyl group, and n represents 2 to 1,000.

12. The oxygenator of claim 11, wherein the number-average molecular weight of the (meth)acrylate copolymer comprising the hydrophobic (meth)acrylate and the hydrophilic (meth)acrylate is from 2,000 to 200,000.

13. The oxygenator of claim 2, wherein the oxygenator is an internal perfusion type oxygenator in which the inner surface of the hollow fiber membranes to contact blood during use is coated with the (meth)acrylate copolymer.

14. The oxygenator of claim 13, wherein the number-average molecular weight of the (meth)acrylate copolymer comprising the hydrophobic (meth)acrylate and the hydrophilic (meth)acrylate is from 2,000 to 200,000.

15. The oxygenator of claim 3, wherein the oxygenator is an internal perfusion type oxygenator in which the inner surface of the hollow fiber membranes to contact blood during use is coated with the (meth)acrylate copolymer.

16. The oxygenator of claim 15, wherein the number-average molecular weight of the (meth)acrylate copolymer comprising the hydrophobic (meth)acrylate and the hydrophilic (meth)acrylate is from 2,000 to 200,000.

17. The oxygenator of claim 2, wherein the oxygenator is an external perfusion type oxygenator in which the outer surface of the hollow fiber membranes to contact blood during use is coated with the (meth)acrylate copolymer.

18. The oxygenator of claim 17, wherein the number-average molecular weight of the (meth)acrylate copolymer comprising the hydrophobic (meth)acrylate and the hydrophilic (meth)acrylate is from 2,000 to 200,000.

19. The oxygenator of claim 3, wherein the oxygenator is an external perfusion type oxygenator in which the outer surface of the hollow fiber membranes to contact blood during use is coated with the (meth)acrylate copolymer.

20. The oxygenator of claim 19, wherein the number-average molecular weight of the (meth)acrylate copolymer comprising the hydrophobic (meth)acrylate and the hydrophilic (meth)acrylate is from 2,000 to 200,000.

* * * * *